US010562948B2

(12) United States Patent
Rutkoski et al.

(10) Patent No.: US 10,562,948 B2
(45) Date of Patent: Feb. 18, 2020

(54) GM-CSF VARIANTS AND METHODS OF USE

(71) Applicant: Janssen Biotech, Inc., Horsham, PA (US)

(72) Inventors: Thomas Rutkoski, Ambler, PA (US); Alexey Teplyakov, Phoenixville, PA (US); Nicole Wunderler, Macungie, PA (US)

(73) Assignee: Janssen Biotech, Inc., Horsham, PA (US)

( * ) Notice: Subject to any disclaimer, the term of this patent is extended or adjusted under 35 U.S.C. 154(b) by 16 days.

(21) Appl. No.: 15/616,216

(22) Filed: Jun. 7, 2017

(65) Prior Publication Data

US 2017/0355742 A1 Dec. 14, 2017

Related U.S. Application Data

(60) Provisional application No. 62/347,342, filed on Jun. 8, 2016, provisional application No. 62/374,068, filed on Aug. 12, 2016, provisional application No. 62/423,857, filed on Nov. 18, 2016.

(51) Int. Cl.
*C07K 14/535* (2006.01)
*A61K 38/19* (2006.01)
*A61K 45/06* (2006.01)

(52) U.S. Cl.
CPC .......... *C07K 14/535* (2013.01); *A61K 38/193* (2013.01); *A61K 45/06* (2013.01)

(58) Field of Classification Search
None
See application file for complete search history.

(56) References Cited

U.S. PATENT DOCUMENTS

2004/0092717 A1 5/2004 Carr et al.
2006/0228417 A1 10/2006 Hubert et al.
2014/0030225 A1* 1/2014 Cox ....................... A61K 47/60 424/85.6
2014/0044672 A1 2/2014 Bossard et al.

FOREIGN PATENT DOCUMENTS

WO WO 2007/009208 A1 1/2007
WO WO-2014116937 A1 * 7/2014 ....... C07K 14/43522

OTHER PUBLICATIONS

Akasako, et al., "High Resistance of *Escherichia coli* Ribonuclease HI Variant with Quintuple Thermostabilizing Mutations to Thermal Denaturation, Acid Denaturation, and Proteolytic Degradation," Biochemistry, 34: 8115-8122 (1995).
Amidon, et al., "Colon-Targeted Oral Drug Delivery Systems: Design Trends and Approaches," AAPS PharmSciTech, 16 (4): 731-741 (2015).
Bernstein, et al., "The Incidence of Deep Venous Thrombosis and Pulmonary Embolism among Patients with Inflammatory Bowel Disease: A Population-based Cohort Study," Throm. Haemost, 85: 430-434 (2001).
Bernstein, et al., "The Incidence of Arterial Thromboembolic Diseases in Inflammatory Bowel DiseaseL A Population-Based Study," Clinical Gastroenterology and Hepatology, 6: 41-45 (2008).
Collins, et al., "Interaction of Recombinant Granulocyte Colony Stimulating Factor with Lipid Membranes: Enhanced Stability of a Wter-Soluble Protein after Membrane Insertion," Biochemistry, 33: 4521-4526 (1994).
Jan Däbritz, "Granulocyte macrophage colony-stimulating factor and the intestinal innate immune cell homeostasis in Crohn's disease," A. J. Physiol. Gastrointest. Liver Physiol. 306: G455-G465 (2014).
Daniel, et al., "A correlation between protein thermostability and resistance to proteolysis," Biochem. J., 207: 641-644 (1982).
Dieckgraefe, et al., "Treatment of active Crohn's disease with recombinant human granulocyte-macrophage colony-stimulating factor," The Lancet, 360: 1478-1480 (2002).
Genzyme Leukine® (sargramostim) Prescribing Information Rx only.
Hansen, et al., "The Structure of the GM-CSF Receptor Complex Reveals a Distinct Mode of Cytokine Receptor Activation," Cell, 134: 496-507 (2008).
Heinzelman, et al., "Engineering superactive granulocyte macrophage colony-stimulating factor transferrin fusion proteins as orally-delivered candidate agents for treating neurodegenerative disease," Biotechnology Progress, 31 (3): 668-677 (2015).
Hercus, et al., "Identification of Residues in the First and Fourth Helices of Human Granulocyte-Macrophage Colony-Stimulating Factor Involved in Biologic Activity and in Binding to the α- and β-Chains of Its Receptor," Blood, 83 (12): 3500-3508 (1994).
Jensen-Pippo, et al., "Enteral Bioavailability of Human Granulocyte Colony Stimulating Factor Conjugated with Poly(ethylene glycol)," Pharmaceutical Research, 13 (1): 102-107 (1996).
Kelsen, et al., "Phase I Trial of Sargramostim in Pediatric Crohn's Disease," Inflammatory Bowel Disease, 16: 1203-1208 (2010).
Korzenik, et al., "Sargramostim for Active Crohn's Disease," The New England Journal of Medicine, 352: 2193-2201 (2005).
Korzenik, et al., "Is Crohn's Disease an Immunodeficiency?" Digestive Diseases and Sciences, 45 (6): 1121-1129 (2000).
Lehmann, et al., "From DNA sequence to improved functionality: using protein sequence comparisons to rapidly design a thermostable consensus phytase," Protein Engineering, 13 (1): 49-57 (2000).
Lehmann, et al., "Engineering proteins for thermostability: the use of sequence alignments versus rational design and directed evolution," Current Opinion in Biotechnology, 12: 371-375 (2001).

(Continued)

*Primary Examiner* — Joanne Hama
*Assistant Examiner* — Jegatheesan Seharaseyon
(74) *Attorney, Agent, or Firm* — Eric Dichter

(57) ABSTRACT

GM-CSF variants, polynucleotides encoding them, and methods of making and using the foregoing are useful in treatment of immune-related disorders, such as inflammatory bowel disease (IBD).

6 Claims, 12 Drawing Sheets

Specification includes a Sequence Listing.

(56) References Cited

OTHER PUBLICATIONS

Lehmann, et al., "The consensus concept for thermostability engineering of proteins," Biochimica et Biophysica Acta, 1543: 408-415 (2000).
McLendon, et al., "Is Protein Turnover Thermodynamically Controlled?" The Journal of Biological Chemistry, 253 (18): 6335-6337 (1978).
Mortha, et al., "Microbiota-Dependent Crosstalk Between Macrophages and ILC3 Promotes Intestinal Homeostasis," Science, 343: 1439-1440 (2014).
Parsell, et al., "The Structural Stability of a Protein Is an Important Determinant of Its Proteolysic Susceptibility in *Escherichia coli*," The Journal of Biological Chemistry, 264 (13): 7590-7595 (1989).
Roth, et al., "Sargramostim (GM-CSF) for Induction of Remission in Crohn's Disease: A Cochrane Inflammatory Bowel Disease and Functional Bowel Disorders Systemic Review of Randomized Trials," Inflammatory Bowel Disease, 18: 1333-1339 (2012).
Rozwarski, et al., "Refined Crystal Structure and Mutagenesis of Human Granulocyte-Macrophage Colony-Stimulating Factor," Proteins, 26 (3): 304-313 (1996).
Valentine, et al., "Steroid-sparing properties of sargramostim in patients with corticosteroid-dependent Crohns' disease: a randomized, double-blind, placebo-controlled, phase 2 study," Gut, 58: 1354-1362 (2009).
Vaughan, et al., "Treatment of Fistulas with Granulocyte Colony-Stimulating Factor in a Patient with Crohn's Disease," The New England Journal of Medicine, 340 (3): 239-240.

* cited by examiner

Figure 2A.

```
        1                            30
1       APARSPSPSTQPWEHVNAIQEARRLLNLSR
2       APARSPSPSTQPWEHVNAIQEARRLLNLCR
3       APARSPSPSTQPWEHVNAIQEARRLLNLSR
4       APARSPSPSTQPWEHVNAIQEARRLLNLSR
5       APARSPSPSTQPWEHVNAIQEALRLLNLSR
6       APARSPSPSTQPWEHVNAIQEARRLLNLCR
7       APARSPSPSTQPWEHVNAIQEARRLLNLCR
8       APARSPSPSTQPWEHVNAIQEALRLLNLCR
9       APARSPSPSTQPWEHVNAIQEARRLLNLCR
        ********************** *****.*
```

```
        31                           60
1       DTAAEMNETVEVISEMFDLQEPTCLQTRLE
2       DTAAEMNETVEVISEMFDLQEPTCLQTRLE
3       DTAAEMNETVEVISEMFDPQEPTCLQTRLE
4       DTAAEMNETVEVISEMFDLQEPTCLQTRLE
5       DTAAEMNETVEVISEMFDLQEPTCLQTRLE
6       DTAAEMNETVEVISEMFDPQEPTCLQTRLE
7       DTAAEMNETVEVISEMFDLQEPTCLQTRLE
8       DTAAEMNETVEVISEMFDPQEPTCLQTRLE
9       DTAAEMNETVEVISEMFDPQEPTCLQTRLE
        ****************** ***********
```

Figure 2B.

```
      61                            90
1     LYKQGLRGSLTKLKGPLTMMASHYKQHCPP
2     LYKQGLRGCLTKLKGPLTMMASHYKQHCPP
3     LYKQGLRGSLTKLKGPLTMMASHYKQHCPP
4     LYKQGLRGSLTKLKGPLTMMASHYKQHCPP
5     LYKQGLRGSLTKLKGPLTMMASHYKQHCPP
6     LYKQGLRGCLTKLKGPLTMMASHYKQHCPP
7     LYKQGLRGCLTKLKGPLTMMASHYKQHCPP
8     LYKQGLRGCLTKLKGPLTMMASHYKQHCPP
9     LYKQGLRGCLTKLKGPLTMMASHYKQHCPP
      ********.*********************

      91                                 127
1     TPETSCATQIITFESFKENLKDFLLVIPFDCWEPVQE
2     TPETSCATQIITFESFKENLKDFLLVIPFDCWEPVQE
3     TPETSCATQIITFESFKENLKDFLLVIPFDCWEPVQE
4     TPETSCATQIITFESFIENLKDFLLVIPFDCWEPVQE
5     TPETSCATQIITFESFKENLKDFLLVIPFDCWEPVQE
6     TPETSCATQIITFESFKENLKDFLLVIPFDCWEPVQE
7     TPETSCATQIITFESFIENLKDFLLVIPFDCWEPVQE
8     TPETSCATQIITFESFIENLKDFLLVIPFDCWEPVQE
9     TPETSCATQIITFESFIENLKDFLLVIPFDCWEPVQE
      **************** ********************
```

GM-CSF VARIANTS AND METHODS OF USE

CROSS-REFERENCE TO RELATED APPLICATIONS

This application claims the benefit of U.S. Provisional Application Ser. No. 62/347,342 filed 8 Jun. 2016, U.S. Provisional Application Ser. No. 62/374,068, filed 12 Aug. 2016, and U.S. Provisional Application Ser. No. 62/423,857, filed 18 Nov. 2016, the entire contents of the aforementioned applications are incorporated herein by reference in their entireties.

SEQUENCE LISTING

This application contains a Sequence Listing submitted via EFS-Web, the entire content incorporated herein by reference in its entirety. The ASCII text file, created on 23 May 2017, is named JBI5088USNP_ST25.txt and is 23 kilobytes in size.

FIELD OF THE INVENTION

The present invention relates to GM-CSF variants, synthetic polynucleotides encoding them, and methods of making and using the foregoing

BACKGROUND OF THE INVENTION

Inflammatory bowel disease (IBD) is a disorder of unknown etiology characterized typically by diarrhea, cramping, abdominal pains, weight loss and rectal bleeding, tiredness, anemia, fistulae, perforations, obstruction of the bowel and frequent need for surgical intervention. According to the US Center for Disease Control and Prevention, about 1.4 million people in USA suffer from IBD, making it one of the most prevalent gastrointestinal diseases in the United States. The overall healthcare cost of IBD in USA is estimated to be more than US$1.7 billion per year.

A number of disorders fall within the class of IBD, including Crohn's disease, ulcerative colitis, indeterminate colitis, microscopic colitis and collagenous colitis. The most common forms of IBD are Crohn's disease and ulcerative colitis. Ulcerative colitis affects the large intestine (colon) and rectum and involves the inner lining (e.g., the mucosal and sub-mucosal layer) of the intestinal wall. Crohn's disease may affect any section of the gastrointestinal tract (e.g., mouth, esophagus, stomach, small intestine, large intestine, rectum, anus, etc.) and may involve all layers of the intestinal wall. The clinical symptoms of IBD include rectal and/or intestinal bleeding, abdominal pain and cramping, diarrhea, and weight loss. In addition, IBD is a risk factor for colon cancer, and this risk for colon cancer increases significantly after eight to ten years of IBD.

IBD has no cure. Current therapies are directed at reducing the inflammatory process and at reducing the detrimental effects of the inflammatory process associated with the disease, and include administration of anti-inflammatory drugs (e.g., APRISO® (mesalamine), AZULFIDINE® (sulfasalazine), REMICADE® (infliximab), HUMIRA® (adalimumab), prednisone, budesonide) and of immunosuppressive drugs (e.g., 6-mercaptopurine, azathioprine, cyclosporine). Such therapies may be associated with adverse side effects, such as nausea, vomiting, anorexia, dyspepsia, malaise, headaches, abdominal pain, fever, rash, pancreatitis, bone marrow suppression, formation of antibodies, infusion reactions, and increased opportunistic infections.

Therefore, a need exists for additional therapies for IBD.

SUMMARY OF THE INVENTION

The invention provides an isolated GM-CSF variant comprising a substitution S29C and a substitution S69C when compared to the wild type GM-CSF of SEQ ID NO: 1, optionally further comprising at least one substitution at an amino acid residue position corresponding to residue R23, L49 or K107 of SEQ ID NO: 1.

The invention also provides an isolated GM-CSF variant comprising an amino acid sequence of SEQ ID NO: 33.

The invention also provides an isolated GM-CSF variant comprising an amino acid sequence of SEQ ID NOs: 2, 3, 4, 6, 7, 8 or 9.

The invention also provides an isolated GM-CSF variant comprising a substitution S29C and a substitution S69C when compared to the wild type GM-CSF of SEQ ID NO: 1, optionally further comprising at least one substitution at an amino acid residue position corresponding to residue R23, L49 or K107 of SEQ ID NO: 1, wherein the GM-CSF variant is conjugated to a half-life extending moiety.

The invention also provides an isolated polynucleotide encoding the GM-CSF variant of the invention.

The invention also provides a vector comprising the polynucleotide of the invention.

The invention also provides an expression vector comprising the polynucleotide of the invention.

The invention also provides a host cell comprising the vector of the invention.

The invention also provides a host cell comprising the expression vector of the invention.

The invention also provides a method of producing the GM-CSF variant of the invention, comprising culturing the host cell of the invention in conditions that the GM-CSF variant is expressed, and purifying the GM-CSF variant.

The invention also provides a kit comprising the GM-CSF variant of the invention.

The invention also provides a pharmaceutical composition comprising the GM-CSF variant of the invention and a pharmaceutically acceptable excipient.

The invention also provides a method of treating an inflammatory bowel disease (IBD) in a subject in need thereof, comprising administering to the subject a therapeutically effective amount of the GM-CSF variant of the invention for a time sufficient to treat the IBD.

BRIEF DESCRIPTION OF THE DRAWINGS

FIG. 2A shows the amino acid sequence alignments between various GM-CSF variants from residues 1-60. The number at the beginning of the row indicates the SEQ ID NO: of the amino acid sequence.

FIG. 2B shows the amino acid sequence alignments between various GM-CSF variants from residues 61-127. The number at the beginning of the row indicates the SEQ ID NO: of the amino acid sequence.

DETAILED DESCRIPTION OF THE INVENTION

Figure 1:
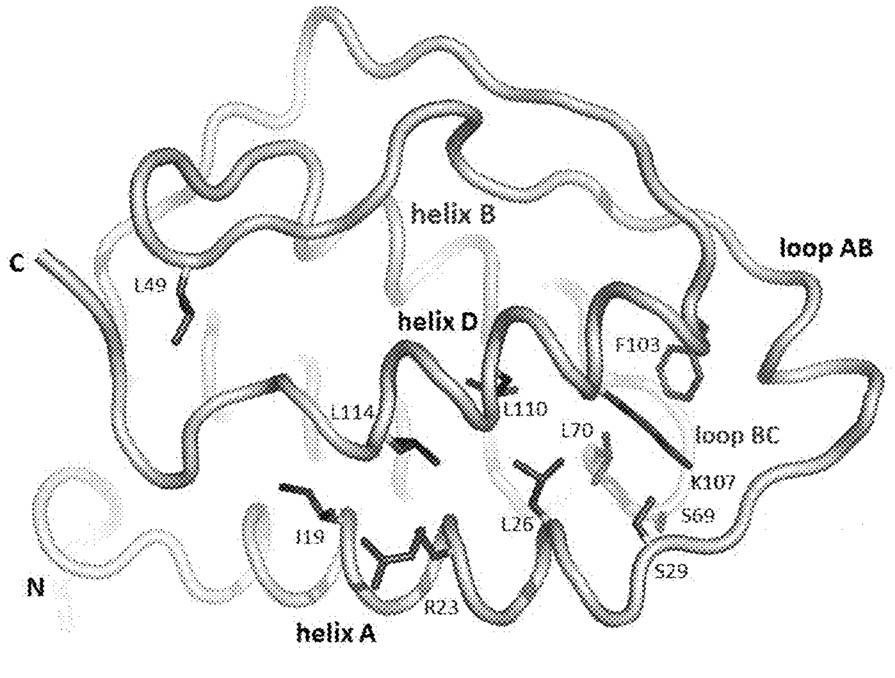
FIG. 1 shows the structure of human GM-CSF (PDB: 2GMF (Rozwarski et al., 1996)) showing the residues considered for engineering to improve stability of GM-CSF.

All publications, including but not limited to patents and patent applications, cited in this specification are herein incorporated by reference as though fully set forth.

As used herein and in the claims, the singular forms “a,” “and,” and “the” include plural reference unless the context clearly dictates otherwise.

Unless defined otherwise, all technical and scientific terms used herein have the same meaning as commonly understood by one of ordinary skill in the art to which an invention belongs. Although any compositions and methods similar or equivalent to those described herein can be used in the practice or testing of the invention, exemplary compositions and methods are described herein.

“Polynucleotide” refers to a molecule comprising a chain of nucleotides covalently linked by a sugar-phosphate backbone or other equivalent covalent chemistry. Double and single-stranded DNA and RNA are typical examples of polynucleotides.

“Polypeptide” or “protein” refers to a molecule that comprises at least two amino acid residues linked by a peptide bond to form a polypeptide.

“Peptide” refers to a short polypeptide up to 30 amino acids long.

“Vector” refers to a polynucleotide capable of being duplicated within a biological system or that can be moved between such systems. Vector polynucleotides typically contain elements, such as origins of replication, polyadenylation signal or selection markers that function to facilitate the duplication or maintenance of these polynucleotides in a biological system, such as a cell, virus, animal, plant, and reconstituted biological systems utilizing biological components capable of duplicating a vector. The vector polynucleotide may be DNA or RNA molecules or a hybrid of these, single stranded or double stranded.

“Expression vector” refers to a vector that can be utilized in a biological system or in a reconstituted biological system to direct the translation of a polypeptide encoded by a polynucleotide sequence present in the expression vector.

“Complementary sequence” refers to a second isolated polynucleotide sequence that is antiparallel to a first isolated polynucleotide sequence and that comprises nucleotides complementary to the nucleotides in the first polynucleotide sequence.

"About" means within an acceptable error range for the value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per the practice in the art, or a range of up to 5%, whichever is larger.

"Sample" refers to a collection of similar fluids, cells, or tissues isolated from a subject, as well as fluids, cells, or tissues present within a subject. Exemplary samples are biological fluids such as blood, serum and serosal fluids, plasma, lymph, urine, saliva, cystic fluid, tear drops, feces, sputum, mucosal secretions of the secretory tissues and organs, vaginal secretions, ascites fluids, fluids of the pleural, pericardial, peritoneal, abdominal and other body cavities, fluids collected by bronchial lavage, synovial fluid, liquid solutions contacted with a subject or biological source, for example, cell and organ culture medium including cell or organ conditioned medium, lavage fluids and the like, tissue biopsies, fine needle aspirations or surgically resected tissue.

"In combination with" means that two or more therapeutics are administered to a subject together in a mixture, concurrently as single agents or sequentially as single agents in any order.

"Subject" includes any human or nonhuman animal "Nonhuman animal" includes all vertebrates, e.g., mammals and non-mammals, such as nonhuman primates, sheep, dogs, cats, horses, cows, chickens, amphibians, reptiles, etc. Except when noted, the terms "patient" and "subject" are used interchangeably.

"Variant" refers to a polypeptide or a polynucleotide that differs from a reference polypeptide or a reference polynucleotide by one or more modifications, for example one or more substitutions, insertions or deletions. For example, the variant differs from a wild-type mature GM-CSF polypeptide of SEQ ID NO: 1 or the polynucleotide encoding the wild-type mature GM-CSF having the sequence of SEQ ID NO: 18 by one or more modifications for example, substitutions, insertions or deletions of nucleotides or amino acids.

"Isolated" refers to a homogenous population of molecules (such as synthetic polynucleotides or synthetic polypeptides) which have been substantially separated and/or purified away from other components of the system the molecules are produced in, such as a recombinant cell, as well as a protein that has been subjected to at least one purification or isolation step. "Isolated GM-CSF variant" refers to a GM-CSF variant that is substantially free of other cellular material and/or chemicals and encompasses variants that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% pure.

"Inflammatory bowel disease (IBD)" refers to a disorder or disease characterized by inflammatory activity in the GI tract. IBD includes, but is not limited to, Crohn's disease, ulcerative colitis, Johne's disease, Behçet's syndrome, collagenous colitis, diversion colitis, indeterminate colitis, microscopic colitis, infective colitis, ischaemic colitis, lymphocytic colitis, idiopathic inflammation of the small and/or proximal intestine, IBD-related diarrhea and closely related diseases and disorders of the gastrointestinal tract.

Throughout the specification, residues that are substituted in the GM-CSF variants are numbered corresponding to their position in the wild-type GM-CSF of SEQ ID NO: 1. For example, "S29C" in the specification refers to the substitution of serine at residue position that corresponds to the position 29 in the wild-type GM-CSF of SEQ ID NO: 1 with cysteine.

Abbreviations of natural amino acids are as used herein are shown in Table 1.

TABLE 1

| Amino acid | Three letter code | One letter code |
|---|---|---|
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Compositions of Matter

The present invention provides granulocyte-macrophage colony stimulating factor (GM-CSF) variants having enhanced stability and/or biological activity when compared to the wild-type GM-CSF. The present invention also provides GM-CSF variants having improved stability in the milieu mimicking that of the gastrointestinal track. Therefore, the GM-CSF variants of the present invention may be suitable for oral administration.

The GM-CSF variants of the invention may be used in therapeutic treatment of subjects having inflammatory bowel disease (IBD), or other diseases or conditions in which potentiation of GM-CSF activity is desired. The polynucleotides, vectors and cell lines of the invention are useful in generating the GM-CSF variants of the invention.

GM-CSF is a key regulator of intestinal innate immunity (Däbritz, 2014) and plays a role in the maintenance of intestinal barrier integrity. Recent evidence demonstrates that enteric GM-CSF is also involved in maintaining tolerance in the mucosa (Mortha et al., 2014). In some Crohn's disease (CD) patients, the etiology has been hypothesized to be a dysregulation of the innate immune system, specifically insufficiency of neutrophil function and that of other GM-CSF-responsive immune cells (Korzenik & Dieckgraefe, 2000).

Systemic GM-CSF administration has been tested in the clinic for the ability to induce remission in patients with CD (Dieckgraefe & Korzenik, 2002; Kelsen et al., 2010; Korzenik, 2005; Vaughan & Drumm, 1999). Despite some promising early clinical results, some adverse events were found in the GM-CSF treatment group in a Phase II CD trial (Valentine et al., 2009). Further, documented increased risk of thrombosis and pulmonary disorders in IBD patients (Bernstein, Blanchard, Houston, & Wajda, 2001; Bernstein, Wajda, & Blanchard, 2008) may also be exacerbated by systemic GM-CSF therapy.

Orally administered GM-CSF for local GI delivery could prove more desirable from a patient compliance as well as from a safety perspective by minimizing systemic exposure. However, oral delivery of protein to the lower gastrointestinal tract presents challenges owing to the harsh pH, proteolytic, and microbial environments to which the biologic drug would be exposed (Amidon, Brown, & Dave, 2015). Indeed, four-helix bundle growth factors similar to that of GM-CSF have been demonstrated to be rapidly degraded by digestive proteases in vitro (Jensen-Pippo, Whitcomb, DePrince, Ralph, & Habberfield, 1996).

The invention also provides an isolated GM-CSF variant comprising a substitution S29C and a substitution S69C when compared to the wild type GM-CSF of SEQ ID NO: 1, optionally further comprising at least one substitution at an amino acid residue position corresponding to a residue R23, L49 or K107 of SEQ ID NO: 1.

The invention also provides an isolated GM-CSF variant comprising an amino acid sequence of SEQ ID NO: 33. SEQ ID NO: 33 is a consensus sequence of GM-CSF variant having S29C and S69C substitutions and optionally substitutions at residue positions R23, L49 or K107.

SEQ ID NO: 33

$APARSPSPSTQPWEHVNAIQEAX_1RLLNLCRDTAAEMNETVEVISEMFD$ $X_2QEPTCLQTRLELYKQGLRGCLTKLKGPLTMMASHYKQHCPPTPETSC$ $ATQIITFESFX_3ENLKDFLLVIPFDCWEPVQE$;

wherein $X_1$ is R or L;

$X_2$ is L or P; and $X_3$ is K or I.

The GM-CSF variant comprising the S29C substitution and the S69C substitution is more stable and more potent when compared to the wild-type GM-CSF. The substitutions create a novel disulfide bond that links GM-CSF loop AB and loop BC.

Exemplary GM-CSF variants with the S29C substitution and the S69C substitution are variants having the amino acid sequence of SEQ ID NOs: 2, 6, 7, 8 and 9.

The invention also provides an isolated GM-CSF variant comprising a substitution S29C and a substitution S69C when compared to the wild type GM-CSF of SEQ ID NO: 1, optionally further comprising at least one substitution at an amino acid residue position corresponding to residue R23, L49 or K107 of SEQ ID NO: 1, wherein the variant exhibits at least about 5° C. higher melting temperature ($T_m$) when compared to that of the wild-type GM-CSF, wherein the $T_m$ is measured using differential scanning calorimetry using a protocol described in Example 1.

GM-CSF variants having higher $T_m$ (e.g. increased thermal stability) are expected to have improved resistant to proteolysis, as it is well established that increased thermal stability generally translates to improved resistance to proteolysis (Akasako, Haruki, Oobatake, & Kanaya, 1995; Daniel, Cowan, Morgan, & Curran, 1982; McLendon & Radany, 1978; Parsell & Sauer, 1989).

The invention also provides an isolated GM-CSF variant comprising a substitution S29C and a substitution S69C when compared to the wild type GM-CSF of SEQ ID NO: 1, optionally further comprising at least one substitution at an amino acid residue position corresponding to residue R23, L49 or K107 of SEQ ID NO: 1, wherein the variant stimulates proliferation of TF-1 ATCC® CRL 2003™ cells with an $EC_{50}$ value that is at least about 1.5-fold less when compared to the $EC_{50}$ value of stimulation of proliferation of the TF-1 ATCC® CRL 2003™ cells with the wild-type GM-CSF using a protocol described in Example 1.

GM-CSF variants having a lower $EC_{50}$ value for their effect in inducing TF-1 cell proliferation when compared to the wild-type GM-CSF in are more potent activators of GM-CSF signaling pathways.

In some embodiments, the substitution at the amino acid residue position corresponding to residue R23 of SEQ ID NO: 1 is a R23A substitution.

In some embodiments, the substitution at the amino acid residue position corresponding to residue R23 of SEQ ID NO: 1 is a R23D substitution.

In some embodiments, the substitution at the amino acid residue position corresponding to residue R23 of SEQ ID NO: 1 is a R23E substitution.

In some embodiments, the substitution at the amino acid residue position corresponding to residue R23 of SEQ ID NO: 1 is a R23F substitution.

In some embodiments, the substitution at the amino acid residue position corresponding to residue R23 of SEQ ID NO: 1 is a R23G substitution.

In some embodiments, the substitution at the amino acid residue position corresponding to residue R23 of SEQ ID NO: 1 is a R23H substitution.

In some embodiments, the substitution at the amino acid residue position corresponding to residue R23 of SEQ ID NO: 1 is a R231 substitution.

In some embodiments, the substitution at the amino acid residue position corresponding to residue R23 of SEQ ID NO: 1 is a R23K substitution.

In some embodiments, the substitution at the amino acid residue position corresponding to residue R23 of SEQ ID NO: 1 is a R23L substitution.

In some embodiments, the substitution at the amino acid residue position corresponding to residue R23 of SEQ ID NO: 1 is a R23M substitution.

In some embodiments, the substitution at the amino acid residue position corresponding to residue R23 of SEQ ID NO: 1 is a R23N substitution.

In some embodiments, the substitution at the amino acid residue position corresponding to residue R23 of SEQ ID NO: 1 is a R23P substitution.

In some embodiments, the substitution at the amino acid residue position corresponding to residue R23 of SEQ ID NO: 1 is a R23Q substitution.

In some embodiments, the substitution at the amino acid residue position corresponding to residue R23 of SEQ ID NO: 1 is a R23S substitution.

In some embodiments, the substitution at the amino acid residue position corresponding to residue R23 of SEQ ID NO: 1 is a R23T substitution.

In some embodiments, the substitution at the amino acid residue position corresponding to residue R23 of SEQ ID NO: 1 is a R23V substitution.

In some embodiments, the substitution at the amino acid residue position corresponding to residue R23 of SEQ ID NO: 1 is a R23W substitution.

In some embodiments, the substitution at the amino acid residue position corresponding to residue R23 of SEQ ID NO: 1 is a R23Y substitution.

In some embodiments, the substitution at the amino acid residue position corresponding to residue L49 of SEQ ID NO: 1 is a L49A substitution.

In some embodiments, the substitution at the amino acid residue position corresponding to residue L49 of SEQ ID NO: 1 is a L49D substitution.

In some embodiments, the substitution at the amino acid residue position corresponding to residue L49 of SEQ ID NO: 1 is a L49E substitution.

In some embodiments, the substitution at the amino acid residue position corresponding to residue L49 of SEQ ID NO: 1 is a L49F substitution.

In some embodiments, the substitution at the amino acid residue position corresponding to residue L49 of SEQ ID NO: 1 is a L49G substitution.

In some embodiments, the substitution at the amino acid residue position corresponding to residue L49 of SEQ ID NO: 1 is a L49H substitution.

In some embodiments, the substitution at the amino acid residue position corresponding to residue L49 of SEQ ID NO: 1 is a L491 substitution.

In some embodiments, the substitution at the amino acid residue position corresponding to residue L49 of SEQ ID NO: 1 is a L49K substitution.

In some embodiments, the substitution at the amino acid residue position corresponding to residue L49 of SEQ ID NO: 1 is a L49M substitution.

In some embodiments, the substitution at the amino acid residue position corresponding to residue L49 of SEQ ID NO: 1 is a L49N substitution.

In some embodiments, the substitution at the amino acid residue position corresponding to residue L49 of SEQ ID NO: 1 is a L49P substitution.

In some embodiments, the substitution at the amino acid residue position corresponding to residue L49 of SEQ ID NO: 1 is a L49Q substitution.

In some embodiments, the substitution at the amino acid residue position corresponding to residue L49 of SEQ ID NO: 1 is a L49R substitution.

In some embodiments, the substitution at the amino acid residue position corresponding to residue L49 of SEQ ID NO: 1 is a L49S substitution.

In some embodiments, the substitution at the amino acid residue position corresponding to residue L49 of SEQ ID NO: 1 is a L49T substitution.

In some embodiments, the substitution at the amino acid residue position corresponding to residue L49 of SEQ ID NO: 1 is a L49V substitution.

In some embodiments, the substitution at the amino acid residue position corresponding to residue L49 of SEQ ID NO: 1 is a L49W substitution.

In some embodiments, the substitution at the amino acid residue position corresponding to residue L49 of SEQ ID NO: 1 is a L49Y substitution.

In some embodiments, the substitution at the amino acid residue position corresponding to residue K107 of SEQ ID NO: 1 is a K107A substitution.

In some embodiments, the substitution at the amino acid residue position corresponding to residue K107 of SEQ ID NO: 1 is a K107D substitution.

In some embodiments, the substitution at the amino acid residue position corresponding to residue K107 of SEQ ID NO: 1 is a K107E substitution.

In some embodiments, the substitution at the amino acid residue position corresponding to residue K107 of SEQ ID NO: 1 is a K107F substitution.

In some embodiments, the substitution at the amino acid residue position corresponding to residue K107 of SEQ ID NO: 1 is a K107G substitution.

In some embodiments, the substitution at the amino acid residue position corresponding to residue K107 of SEQ ID NO: 1 is a K107H substitution.

In some embodiments, the substitution at the amino acid residue position corresponding to residue K107 of SEQ ID NO: 1 is a K107I substitution.

In some embodiments, the substitution at the amino acid residue position corresponding to residue K107 of SEQ ID NO: 1 is a K107L substitution.

In some embodiments, the substitution at the amino acid residue position corresponding to residue K107 of SEQ ID NO: 1 is a K107M substitution.

In some embodiments, the substitution at the amino acid residue position corresponding to residue K107 of SEQ ID NO: 1 is a K107N substitution.

In some embodiments, the substitution at the amino acid residue position corresponding to residue K107 of SEQ ID NO: 1 is a K107P substitution.

In some embodiments, the substitution at the amino acid residue position corresponding to residue K107 of SEQ ID NO: 1 is a K107Q substitution.

In some embodiments, the substitution at the amino acid residue position corresponding to residue K107 of SEQ ID NO: 1 is a K107R substitution.

In some embodiments, the substitution at the amino acid residue position corresponding to residue K107 of SEQ ID NO: 1 is a K107S substitution.

In some embodiments, the substitution at the amino acid residue position corresponding to residue K107 of SEQ ID NO: 1 is a K107T substitution.

In some embodiments, the substitution at the amino acid residue position corresponding to residue K107 of SEQ ID NO: 1 is a K107V substitution.

In some embodiments, the substitution at the amino acid residue position corresponding to residue K107 of SEQ ID NO: 1 is a K107W substitution.

In some embodiments, the substitution at the amino acid residue position corresponding to residue K107 of SEQ ID NO: 1 is a K107Y substitution.

In some embodiments, the GM-CSF variant comprises a R23L substitution, a L49P substitution and a K107I substitution. These substitutions improve thermal stability and potency of the GM-CSF variant. In addition, the L49P substitution removes a potential MHC class II epitope and therefore the GM-CSF variants with the L49P substitution may be less immunogenic.

In some embodiments, the GM-CSF variant comprises the S29C substitution, the S69C substitution and the R23L substitution. These substitutions improve thermal stability and potency of the GM-CSF variant.

In some embodiments, the GM-CSF variant comprises the S29C substitution, the S69C substitution and the L49P substitution. These substitutions improve thermal stability and potency of the GM-CSF variant. In addition, the L49P substitution removes a potential MHC class II epitope and therefore the GM-CSF variants with the L49P substitution may be less immunogenic.

In some embodiments, the GM-CSF variant comprises the S29C substitution, the S69C substitution and the K107I substitution. These substitutions improve thermal stability and potency of the GM-CSF variant.

In some embodiments, the GM-CSF variant comprises the S29C substitution, the S69C substitution, the R23L substitution and the L49P substitution. These substitutions improve thermal stability of the GM-CSF variant. In addition, the L49P substitution removes a potential MHC class II epitope and therefore the GM-CSF variants with the L49P substitution may be less immunogenic.

In some embodiments, the GM-CSF variant comprises the S29C substitution, the S69C substitution, the R23L substitution and the K107I substitution. These substitutions improve thermal stability of the GM-CSF variant.

In some embodiments, the GM-CSF variant comprises the S29C substitution, the S69C substitution, the L49P substitution and a K107I substitution. These substitutions improve thermal stability and potency of the GM-CSF variant. In addition, the L49P substitution removes a potential MHC class II epitope and therefore the GM-CSF variants with the L49P substitution may be less immunogenic.

In some embodiments, the GM-CSF variant comprises the S29C substitution, the S69C substitution, the R23L substitution, the L49P substitution and the K107I substitution. These substitutions improve thermal stability and potency of the GM-CSF variant. In addition, the L49P substitution removes a potential MHC class II epitope and therefore the GM-CSF variants with the L49P substitution may be less immunogenic.

In some embodiments, the GM-CSF variant comprises a substitution at an amino acid residue position corresponding to residue R23 of SEQ ID NO: 1.

In some embodiments, the GM-CSF variant comprises a substitution at an amino acid residue position corresponding to residue L49 of SEQ ID NO: 1.

In some embodiments, the GM-CSF variant comprises a substitution at an amino acid residue position corresponding to residue K107 of SEQ ID NO: 1.

In some embodiments, the GM-CSF variant comprises a R23L substitution. The substitution improves thermal stability and potency of the GM-CSF variant.

In some embodiments, the GM-CSF variant comprises a L49P substitution. The substitution improves thermal stability of the GM-CSF variant and removes a potential MHC class II epitope and therefore the GM-CSF variants with the L49P substitution may be less immunogenic.

In some embodiments, the GM-CSF variant comprises a K107I substitution. The substitution improves thermal stability of the GM-CSF variant.

In some embodiments, the GM-CSF variant comprises a R23L substitution and a L49P substitution. These substitutions improve thermal stability and potency of the GM-CSF variant. In addition, the L49P substitution removes a potential MHC class II epitope and therefore the GM-CSF variants with the L49P substitution may be less immunogenic.

In some embodiments, the GM-CSF variant comprises a R23L substitution and a K107I substitution. These substitutions improve thermal stability and potency of the GM-CSF variant.

In some embodiments, the GM-CSF variant comprises a L49P substitution and a K107I substitution. These substitutions improve thermal stability and potency of the GM-CSF variant. In addition, the L49P substitution removes a potential MHC class II epitope and therefore the GM-CSF variants with the L49P substitution may be less immunogenic.

In some embodiments, the GM-CSF variant comprises the amino acid sequence of SEQ ID NO: 2.

In some embodiments, the GM-CSF variant is encoded by a polynucleotide comprising the polynucleotide sequence of SEQ ID NO: 10.

In some embodiments, the GM-CSF variant comprises the amino acid sequence of SEQ ID NO: 3.

In some embodiments, the GM-CSF variant is encoded by a polynucleotide comprising the polynucleotide sequence of SEQ ID NO: 11.

In some embodiments, the GM-CSF variant comprises the amino acid sequence of SEQ ID NO: 4.

In some embodiments, the GM-CSF variant is encoded by a polynucleotide comprising the polynucleotide sequence of SEQ ID NO: 12.

In some embodiments, the GM-CSF variant comprises the amino acid sequence of SEQ ID NO: 5.

In some embodiments, the GM-CSF variant is encoded by a polynucleotide comprising the polynucleotide sequence of SEQ ID NO: 13.

In some embodiments, the GM-CSF variant comprises the amino acid sequence of SEQ ID NO: 6.

In some embodiments, the GM-CSF variant is encoded by a polynucleotide comprising the polynucleotide sequence of SEQ ID NO: 14.

In some embodiments, the GM-CSF variant comprises the amino acid sequence of SEQ ID NO: 7.

In some embodiments, the GM-CSF variant is encoded by a polynucleotide comprising the polynucleotide sequence of SEQ ID NO: 15.

In some embodiments, the GM-CSF variant comprises the amino acid sequence of SEQ ID NO: 8.

In some embodiments, the GM-CSF variant is encoded by a polynucleotide comprising the polynucleotide sequence of SEQ ID NO: 16.

In some embodiments, the GM-CSF variant comprises the amino acid sequence of SEQ ID NO: 9.

In some embodiments, the GM-CSF variant is encoded by a polynucleotide comprising the polynucleotide sequence of SEQ ID NO: 17.

The GM-CSF variants of the invention may be obtained from polynucleotides encoding the GM-CSF variants by the use of cell-free expression systems such as reticulocyte lysate based expression systems, or by standard recombinant expression systems. For example, the polynucleotides encoding the GM-CSF variants may be synthesized using chemical gene synthesis according to methods described in U.S. Pat. Nos. 6,521,427 and 6,670,127, utilizing degenerate oligonucleotides to generate the desired variants, or by standard PCR cloning and mutagenesis. The polynucleotides encoding the GM-CSF variants may be cloned into expression vectors and expressed using standard procedures. The expressed GM-CSF may be purified using for example CaptoQ anion exchange, Capto Phenyl HIC resin and DEAE anion exchange. The generated GM-CSF variants may be tested for their improved thermal stability and potency using assays described for example in Example 1.

Homologous GM-CSF Molecules

Additional substitutions may be made to the GM-CSF variants of the invention as long as the resulting variants comprise a substitution S29C and a substitution S69C when compared to the wild type GM-CSF of SEQ ID NO: 1 and retain or have enhanced thermal stability and/or potency when compared to the parental GM-CSF variant. Thermal stability and potency may be assessed using the protocols described in Example 1.

Additional substitutions that can be made are those that are earlier described:

R24L described in U.S. Pat. No. 5,391,485;

R23L/N27D/T39E/E123K described in U.S. Pat. No. 5,405,952;

Q20A and/or E21A described in Int. Patent Publ. No. WO1989/010403;

substitutions shown in Table 2 and Table 3 and as described in U.S. Pat. No. 7,208,147.

Conservative modifications may also be made to the GM-CSF variants of the invention as long as the resulting variants comprise a substitution S29C and a substitution S69C when compared to the wild type GM-CSF of SEQ ID NO: 1 and retain or have enhanced thermal stability and/or potency when compared to the parental GM-CSF variant.

"Conservative modifications" refer to amino acid modifications that do not significantly affect or alter the characteristics of the molecule containing the amino acid sequences. Conservative modifications include amino acid substitutions, additions and deletions. Conservative substitutions are those in which the amino acid is replaced with an amino acid residue having a similar side chain. The families of amino acid residues having similar side chains are well defined and include amino acids with acidic side chains (e.g., aspartic acid, glutamic acid), basic side chains (e.g., lysine, arginine, histidine), nonpolar side chains (e.g., alanine, valine, leucine, isoleucine, proline, phenylalanine, methionine), uncharged polar side chains (e.g., glycine, asparagine, glutamine, cysteine, serine, threonine, tyrosine, tryptophan), aromatic side chains (e.g., phenylalanine, tryptophan, histidine, tyrosine), aliphatic side chains (e.g., glycine, alanine, valine, leucine, isoleucine, serine, threonine), amide (e.g., asparagine, glutamine), beta-branched side chains (e.g., threonine, valine, isoleucine) and sulfur-containing side chains (cysteine, methionine). Furthermore, any native residue in the polypeptide may also be substituted with alanine, as has been previously described for alanine scanning mutagenesis (MacLennan et al., (1988) *Acta Physiol Scand Suppl* 643:55-67; Sasaki et al., (1988) *Adv Biophys* 35:1-24).

The substitutions may be made individually or combinatorially using known methods. For example, amino acid substitutions to the GM-CSF variants of the invention may be made by known methods for example by PCR mutagenesis (U.S. Pat. No. 4,683,195). Alternatively, libraries of variants may be generated for example using random (NNK) or non-random codons, for example DVK codons, which encode 11 amino acids (Ala, Cys, Asp, Glu, Gly, Lys, Asn, Arg, Ser, Tyr, Trp). The resulting GM-CSF variants may be tested for their thermal stability and potency using protocols described in Example 1.

TABLE 2

| Residue number | Wild-type residue | Possible substitution | | | | | | | | | | | | | |
|---|---|---|---|---|---|---|---|---|---|---|---|---|---|---|---|
| 16 | V | A | C | D | E | G | H | K | N | P | Q | R | S | T | |
| 19 | I | A | C | D | E | G | H | K | N | P | Q | R | S | T | |
| 25 | L | A | C | D | E | G | H | K | N | P | Q | R | S | T | |
| 26 | L | A | C | D | E | G | H | K | N | P | Q | R | S | T | |
| 28 | L | A | C | D | E | F | G | H | K | N | P | Q | R | S | T |
| 36 | M | A | C | D | E | G | H | K | N | P | Q | R | S | T | |
| 40 | V | A | C | D | E | G | H | K | N | P | Q | R | S | T | |
| 43 | I | A | C | D | E | G | H | K | N | P | Q | R | S | T | |
| 46 | M | A | C | D | E | G | H | K | N | P | Q | R | S | T | |
| 47 | F | A | C | D | E | G | H | K | N | P | Q | R | S | T | |
| 49 | L | A | C | D | E | G | H | K | N | P | Q | R | S | T | |
| 55 | L | A | C | D | E | G | H | K | N | P | Q | R | S | T | |
| 59 | L | A | C | D | E | G | H | K | N | P | Q | R | S | T | |
| 61 | L | A | C | D | E | G | H | K | N | P | Q | R | S | T | |
| 62 | Y | A | C | D | E | G | H | K | N | P | Q | R | S | T | |
| 66 | L | A | C | D | E | G | H | K | N | P | Q | R | S | T | |
| 70 | L | A | C | D | E | G | H | K | N | P | Q | R | S | T | |
| 73 | L | A | C | D | E | G | H | K | N | P | Q | R | S | T | |
| 77 | L | A | C | D | E | G | H | K | N | P | Q | R | S | T | |
| 79 | M | A | C | D | E | G | H | K | N | P | Q | R | S | T | |
| 80 | M | A | C | D | E | G | H | K | N | P | Q | R | S | T | |
| 84 | Y | C | D | E | G | H | N | P | R | S | T | | | | |
| 101 | I | A | C | D | E | G | H | K | N | P | Q | R | S | T | |
| 106 | F | A | C | D | E | G | H | K | N | P | Q | R | S | T | |
| 110 | L | A | C | D | E | G | H | K | N | P | Q | R | S | T | |
| 113 | F | A | C | D | E | G | H | K | N | P | Q | R | S | T | |
| 114 | L | A | C | D | E | G | H | K | N | P | Q | R | S | T | |
| 115 | L | A | C | D | E | G | H | K | N | P | Q | R | S | T | |
| 117 | I | A | C | D | E | G | H | K | N | P | Q | R | S | T | |

TABLE 3

| Residue number | Wild-type residue | Possible substitution | | | | | | | | | | | | | |
|---|---|---|---|---|---|---|---|---|---|---|---|---|---|---|---|
| 15 | H | A | C | F | G | I | L | M | P | V | W | Y | | | |
| 18 | A | F | H | K | L | N | P | Q | R | S | T | W | Y | | |
| 20 | Q | T | | | | | | | | | | | | | |
| 21 | E | F | I | P | V | W | Y | | | | | | | | |
| 22 | A | D | E | F | H | I | K | N | P | Q | R | S | T | V | W |
| 24 | R | A | C | F | G | I | L | M | P | V | W | Y | | | |
| 26 | L | F | I | M | V | W | Y | | | | | | | | |
| 31 | D | H | | | | | | | | | | | | | |
| 34 | A | H | K | N | P | Q | R | S | T | V | W | Y | | | |
| 35 | E | A | C | G | P | | | | | | | | | | |
| 36 | M | W | Y | | | | | | | | | | | | |
| 37 | N | A | C | G | P | | | | | | | | | | |
| 38 | E | A | C | G | P | | | | | | | | | | |

TABLE 3-continued

| Residue number | Wild-type residue | Possible substitution | | | | | | | | | | | | | | |
|---|---|---|---|---|---|---|---|---|---|---|---|---|---|---|---|---|
| 42 | V | A | C | D | E | G | H | K | M | N | P | Q | R | S | T | W |
| 45 | E | A | C | F | G | I | L | M | P | V | W | Y | | | | |
| 47 | F | W | | | | | | | | | | | | | | |
| 49 | L | W | Y | | | | | | | | | | | | | |
| 50 | Q | P | | | | | | | | | | | | | | |
| 60 | E | A | C | G | P | | | | | | | | | | | |
| 61 | L | F | I | M | | | | | | | | | | | | |
| 63 | K | A | C | G | I | M | P | Y | | | | | | | | |
| 64 | Q | A | C | G | P | | | | | | | | | | | |
| 66 | L | F | I | M | V | | | | | | | | | | | |
| 67 | R | A | C | G | P | | | | | | | | | | | |
| 69 | S | T | | | | | | | | | | | | | | |
| 70 | L | M | W | | | | | | | | | | | | | |
| 71 | T | A | C | G | P | | | | | | | | | | | |
| 72 | K | T | | | | | | | | | | | | | | |
| 74 | K | T | | | | | | | | | | | | | | |
| 75 | G | H | P | | | | | | | | | | | | | |
| 77 | L | F | I | W | Y | | | | | | | | | | | |
| 78 | T | A | C | G | P | W | Y | | | | | | | | | |
| 82 | S | A | C | F | G | M | P | V | W | Y | | | | | | |
| 85 | K | H | P | | | | | | | | | | | | | |
| 87 | H | A | C | F | G | I | M | P | W | Y | | | | | | |
| 88 | C | D | E | H | K | N | P | Q | R | S | T | W | | | | |
| 109 | N | T | | | | | | | | | | | | | | |
| 121 | C | P | Y | | | | | | | | | | | | | |
| 122 | W | T | | | | | | | | | | | | | | |

Half-Life Extending Moieties

The invention also provides a GM-CSF variant conjugated to a half-life extending moiety.

In some embodiments, the half-life extending moiety is a human serum albumin (HAS), a variant of the human serum albumin, such as a C34S variant, a transthyretin (TTR), a thyroxine-binding globulin (TGB), an albumin-binding domain, or an Fc or fragments thereof. The half-life extending moiety may be conjugated to the N-terminus or to the C-terminus of the GM-CSF variant.

In some embodiments, the half-life extending moiety is conjugated to the N-terminus of GM-CSF.

In some embodiments, the Fc is an IgG1, an IgG2, an IgG3 or an IgG4 isotype.

In some embodiments, the half-life extending moiety is a C34S variant of HSA conjugated to the N-terminus of GM-CSF.

In some embodiments, the half-life extending moiety is a C34S variant of HSA conjugated to the N-terminus of GM-CSF via a linker of SEQ ID NO: 23.

In some embodiments, the half-life extending moiety is a C34S variant of HSA conjugated to the N-terminus of GM-CSF via a linker of SEQ ID NO: 27.

In some embodiments, the half-life extending moiety is a Fc conjugated to the N-terminus of GM-CSF.

In some embodiments, the half-life extending moiety is a Fc conjugated to the N-terminus of GM-CSF via a linker of SEQ ID NO: 23.

In some embodiments, the half-life extending moiety is a Fc conjugated to the N-terminus of GM-CSF via a linker of SEQ ID NO: 27.

In some embodiments, the linker comprises the amino acid sequence of SEQ ID NOs: 20, 21, 22, 23, 24, 25, 26, 27, 28, 29 or 30.

In some embodiments, the Fc comprises at least one substitution. Fc substitutions may be made to the Fc to modulate the effector functions and pharmacokinetic properties of the GM-CSF variant conjugated to the Fc.

Fc positions that may be substituted to modulate the half-life of an Fc containing molecule are those described for example in Dall'Acqua et al., (2006) *J Biol Chem* 281:23514-240, Zalevsky et al., (2010) *Nat Biotechnol* 28:157-159, Hinton et al., (2004) *J Biol Chem* 279(8):6213-6216, Hinton et al., (2006) *J Immunol* 176:346-356, Shields et al. (2001) *J Biol Chem* 276:6591-6607, Petkova et al., (2006). *Int Immunol* 18:1759-1769, Datta-Mannan et al., (2007) *Drug Metab Dispos,* 35:86-94, 2007, Vaccaro et al., (2005) *Nat Biotechnol* 23:1283-1288, Yeung et al., (2010) *Cancer Res,* 70:3269-3277 and Kim et al., (1999) *Eur J Immunol* 29: 2819, and include positions 250, 252, 253, 254, 256, 257, 307, 376, 380, 428, 434 and 435. Exemplary substitutions that may be made singularly or in combination are substitutions T250Q, M252Y, I253A, S254T, T256E, P257I, T307A, D376V, E380A, M428L, H433K, N434S, N434A, N434H, N434F, H435A and H435R. Exemplary singular or combination substitutions that may be made to increase the half-life of the Fc containing molecule are substitutions M428L/N434S, M252Y/S254T/T256E, T250Q/M428L, N434A and T307A/E380A/N434A. Exemplary singular or combination substitutions that may be made to reduce the half-life of the Fc containing molecule are substitutions H435A, P257I/N434H, D376V/N434H, M252Y/S254T/T256E/H433K/N434F, T308P/N434A and H435R.

In some embodiments, the Fc comprises at least one substitution that reduces binding of the Fc containing molecule to an activating Fcγ receptor (FcγR) and/or reduces Fc-mediated effector functions.

Fc positions that may be substituted to reduce binding of the Fc containing molecule to the activating FcγR and subsequently to reduce effector function are those described for example in Shields et al., (2001) *J Biol Chem* 276:6591-6604, Intl. Patent Publ. No. WO2011/066501, U.S. Pat. Nos. 6,737,056 and 5,624,821, Xu et al., (2000) *Cell Immunol,* 200:16-26, Alegre et al., (1994) *Transplantation* 57:1537-1543, Bolt et al., (1993) *Eur J Immunol* 23:403-411, Cole et al., (1999) *Transplantation,* 68:563-571, Rother et al., (2007) *Nat Biotechnol* 25:1256-1264, Ghevaert et al., (2008) *J Clin Invest* 118:2929-2938, An et al., (2009) mAbs, 1:572-579) and include positions 214, 233, 234, 235, 236, 237, 238, 265, 267, 268, 270, 295, 297, 309, 327, 328, 329, 330, 331 and 365. Exemplary substitutions that may be made singularly or in combination are substitutions K214T, E233P, L234V, L234A, deletion of G236, V234A, F234A, L235A, G237A, P238A, P238S, D265A, S267E, H268A, H268Q, Q268A, N297A, A327Q, P329A, D270A, Q295A, V309L, A327S, L328F, A330S and P331S in IgG1, IgG2, IgG3 or IgG4. Exemplary combination substitutions that result in Fc containing molecules with reduced effector functions are substitutions L234A/L235A on IgG1, V234A,/G237A/P238S/H268A/V309L/A330S/P331S on IgG2, F234A/L235A on IgG4, S228P/F234A/L235A on IgG4, N297A on all Ig isotypes, V234A/G237A on IgG2, K214T/E233P/L234V/L235A/G236-deleted/A327G/P331A/D365E/L358M on IgG1, H268Q/V309L/A330S/P331S on IgG2, S267E/L328F on IgG1, L234F/L235E/D265A on IgG1, L234A/L235A/G237A/P238S/H268A/A330S/P331S on IgG1, S228P/F234A/L235A/G237A/P238S on IgG4, and S228P/F234A/L235A/G236-deleted/G237A/P238S on IgG4. Hybrid IgG2/4 Fc domains may also be used, such as Fc with residues 117-260 from IgG2 and residues 261-447 from IgG4.

In some embodiments, the half-life extending moiety is conjugated to the GM-CSF variant via a polypeptide linker. Suitable linkers are for example linkers shown in Table 4.

TABLE 4

| Linker name | Linker AA Sequence | SEQ ID NO: |
|---|---|---|
| 1FU1 | ASLDTTAENQAKNEHLQKENERLLRDWNDVQGRFEKGS | 20 |
| 1DC1(13AA)$_2$ | ASEKNKRSTPYIERAEKNKRSTPYIERAGS | 21 |
| 1DC1(13AA)$_3$ | ASEKNKRSTPYIERAEKNKRSTPYIERAEKNKRSTPYIERAGS | 22 |
| AS(AP)$_{10}$GS | ASAPAPAPAPAPAPAPAPAPAPGS | 23 |
| AS(AP)$_{20}$GS | ASAPAPAPAPAPAPAPAPAPAPAPAPAPAPAPAPAPAPAPAPGS | 24 |
| (EAAAK)$_4$ | ASAEAAAKEAAAKEAAAKEAAAKAGS | 25 |
| (EAAAK)$_8$ | ASAEAAAKEAAAKEAAAKEAAAKEAAAKEAAAKEAAAKEAAAKAGS | 26 |
| GS(G$_4$S)$_4$ | GSGGGGSGGGGSGGGGSGGGGS | 27 |
| GS(G$_4$S)$_8$ | GSGGGGSGGGGSGGGGSGGGGSGGGGSGGGGSGGGGSGGGGS | 28 |
| GS12X(G4S) | GSGGGGSGGGGSGGGGSGGGGSGGGGSGGGGSGGGGSGGGGSGGGGSGGGGSGGGGSGGGGS | 29 |
| GS16X(G4S) | GSGGGGSGGGGSGGGGSGGGGSGGGGSGGGGSGGGGSGGGGSGGGGSGGGGSGGGGSGGGGSGGGGSGGGGSGGGGSGGGGS | 30 |

In some embodiments, the half-life extending moiety is an ethylene glycol, a polyethylene glycol (PEG) molecule, such as PEG5000 or PEG20000, a dextran, a polylysine, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, or carbohydrates (dextran, cellulose, oligo- or polysaccharides. These moieties may be direct fusions with the GM-CSF variant and may be generated by standard cloning and expression techniques. Alternatively, well-known chemical coupling methods may be used to attach the moieties to the GM-CSF variant of the invention.

Polynucleotides, Vectors and Host Cells

The invention also provides polynucleotides encoding the GM-CSF variants of the invention. The polynucleotide may be a complementary deoxynucleic acid (cDNA), and may be codon optimized for expression in suitable host. Codon optimization is a well-known technology.

In some embodiments, the polynucleotide encoding the GM-CSF variant comprises the polynucleotide sequence of SEQ ID NOs: 10, 11, 12, 14, 15, 16 or 17.

The polynucleotide sequences encoding the GM-CSF variants of the invention may be operably linked to one or more regulatory elements, such as a promoter or enhancer, that allow expression of the nucleotide sequence in the intended host cell. The polynucleotide may be cDNA.

The invention also provides a vector comprising the polynucleotide encoding the GM-CSF variant of the invention.

The invention also provides an expression vector comprising the polynucleotide encoding the GM-CSF variant of the invention.

The invention also provides an expression vector comprising the polynucleotide sequence of SEQ ID NO: 10.

The invention also provides an expression vector comprising the polynucleotide sequence of SEQ ID NO: 11.

The invention also provides an expression vector comprising the polynucleotide sequence of SEQ ID NO: 12.

The invention also provides an expression vector comprising the polynucleotide sequence of SEQ ID NO: 13.

The invention also provides an expression vector comprising the polynucleotide sequence of SEQ ID NO: 14.

The invention also provides an expression vector comprising the polynucleotide sequence of SEQ ID NO: 15.

The invention also provides an expression vector comprising the polynucleotide sequence of SEQ ID NO: 16.

The invention also provides an expression vector comprising the polynucleotide sequence of SEQ ID NO: 17.

Such vectors may be plasmid vectors, viral vectors, vectors for baculovirus expression, transposon based vectors or any other vector suitable for introduction of the synthetic polynucleotide of the invention into a given organism or genetic background by any means. For example, polynucleotides encoding the GM-CSF variants of the invention, optionally conjugated to a half-life extending moiety, are inserted into expression vectors. The DNA segments encoding immunoglobulin chains may be operably linked to control sequences in the expression vector(s) that ensure the expression of immunoglobulin polypeptides. Such control sequences include signal sequences, promoters (e.g. naturally associated or heterologous promoters), enhancer elements, and transcription termination sequences, and are chosen to be compatible with the host cell chosen to express the antibody. Once the vector has been incorporated into the appropriate host, the host is maintained under conditions suitable for high level expression of the proteins encoded by the incorporated polynucleotides.

Suitable expression vectors are typically replicable in the host organisms either as episomes or as an integral part of the host chromosomal DNA. Commonly, expression vectors contain selection markers such as ampicillin-resistance, hygromycin-resistance, tetracycline resistance, kanamycin resistance or neomycin resistance to permit detection of those cells transformed with the desired DNA sequences.

Suitable promoter and enhancer elements are known in the art. For expression in a eukaryotic cell, exemplary promoters include light and/or heavy chain immunoglobulin gene promoter and enhancer elements, cytomegalovirus immediate early promoter, herpes simplex virus thymidine kinase promoter, early and late SV40 promoters, promoter present in long terminal repeats from a retrovirus, mouse metallothionein-I promoter, tetracycline-inducible promoter, and various art-known tissue specific promoters. Selection of the appropriate vector and promoter is well known.

An exemplary promoter that can be used comprises the amino acid sequence of SEQ ID NO: 31 and may be encoded by a polynucleotide comprising the polynucleotide sequence of SEQ ID NO: 32.

SEQ ID NO: 31
MAWVWTLLFLMAAAQSIQA

SEQ ID NO: 32
ATGGCCTGGGTGTGGACCCTGCTGTTCCTGATGGCCGCCGCCCAGAGCAT
CCAGGCC

Large numbers of suitable vectors and promoters are known. Many are commercially available for generating recombinant constructs. Exemplary vectors are bacterial vectors pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden), and eukaryotic vectors pWLneo, pSV2cat, pOG44, PXR1, pSG (Stratagene) pSVK3, pBPV, pMSG and pSVL (Pharmacia), pEE6.4 (Lonza) and pEE12.4 (Lonza). Exemplary promoters include light and/or heavy chain immunoglobulin gene promoter and enhancer elements, cytomegalovirus immediate early promoter, herpes simplex virus thymidine kinase promoter, early and late SV40 promoters, promoter present in long terminal repeats from a retrovirus, mouse metallothionein-I promoter, tetracycline-inducible promoter, and various art-known tissue specific promoters. Selection of the appropriate vector and promoter is well known.

The invention also provides a host cell comprising one or more vectors of the invention. "Host cell" refers to a cell into which a vector has been introduced. It is understood that the term host cell is intended to refer not only to the particular subject cell but to the progeny of such a cell, and also to a stable cell line generated from the particular subject cell. Because certain modifications may occur in succeeding generations due to either mutation or environmental influences, such progeny may not be identical to the parent cell, but are still included within the scope of the term "host cell" as used herein. Such host cells may be eukaryotic cells, prokaryotic cells, plant cells or archeal cells. *Escherichia coli*, bacilli, such as *Bacillus subtilis*, and other enterobacteriaceae, such as *Salmonella, Serratia*, and various *Pseudomonas* species are examples of prokaryotic host cells. Other microbes, such as yeast, are also useful for expression. *Saccharomyces* (e.g., *S. cerevisiae*) and Pichia are examples of suitable yeast host cells. Exemplary eukaryotic cells may be of mammalian, insect, avian or other animal origins Mammalian eukaryotic cells include immortalized cell lines such as hybridomas or myeloma cell lines such as SP2/0 (American Type Culture Collection (ATCC), Manassas, Va., CRL-1581), NSO (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1SV (Lonza Biologics, Walkersville, Md.), CHO-K1 (ATCC CRL-61) or DG44.

The invention also provides a method of producing the GM-CSF variant of the invention, comprising culturing the host cell of the invention in conditions that the GM-CSF variant is expressed, and recovering the GM-CSF variant produced by the host cell. Once synthesized (either chemically or recombinantly), the GM-CSF variants may be purified according to standard procedures, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). The GM-CSF variant of the invention may be substantially pure, e.g., at least about 80% to 85% pure, at least about 85% to 90% pure, at least about 90% to 95% pure, or at least about 98% to 99%, or more, pure, e.g., free from contaminants such as cell debris, macromolecules, etc. other than the GM-CSF variant of the invention.

The polynucleotides encoding the GM-CSF variants of the invention may be incorporated into vectors using standard molecular biology methods. Host cell transformation, culture, antibody expression and purification are done using well known methods.

Methods of Use

The GM-CSF variants of the invention have in vitro and in vivo therapeutic and prophylactic utilities. For example, the GM-CSF variants of the invention may be administered to cells in culture, in vitro or ex vivo, or to a subject to treat, prevent, and/or diagnose a variety of disorders, such as inflammatory bowel disease (IBD).

The invention provides a method of treating inflammatory bowel disease (IBD) in a subject in need thereof, comprising administering to the subject a therapeutically effective amount of the GM-CSF variant of the invention for a time sufficient to treat IBD.

In some embodiments, IBD is Crohn's disease.

In some embodiments, IBD is an ulcerative colitis.

In some embodiments, IBD is Johne's disease, Behçet's syndrome, collagenous colitis, diversion colitis, indeterminate colitis, microscopic colitis, infective colitis, ischaemic colitis, lymphocytic colitis, idiopathic inflammation of the small and/or proximal intestine, IBD-related diarrhea and closely related diseases and disorders of the gastrointestinal tract.

In some embodiments, the subject is in remission.

In some embodiments, the subject is resistant to treatment with at least one of the therapeutics an aminosalicylate, a corticosteroid, an immunomodulator, an antibiotic, or a biologic.

The methods of the invention may be used to treat a subject belonging to any animal classification. Examples of subjects that may be treated include mammals such as humans, rodents, dogs, cats and farm animals.

The GM-CSF variants of the invention may be useful in the preparation of a medicament for such treatment, wherein the medicament is prepared for administration in dosages defined herein.

In some embodiments, the GM-CSF variant is administered as an induction therapy.

In some embodiments, the GM-CSF variant is administered as a maintenance therapy.

"Therapeutically effective amount" of the GM-CSF variant of the invention effective in the treatment of IBD may be determined by standard research techniques. Selection of a particular effective dose may be determined (e.g., via clinical trials) by those skilled in the art based upon the consideration of several factors. Such factors include the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems.

"Treat" or "treatment" refers to therapeutic treatment wherein the object is to slow down (lessen) an undesired physiological change or disease, or to provide a beneficial or desired clinical outcome during treatment. Beneficial or desired clinical outcomes include alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" may also mean prolonging survival as compared to expected survival if a subject was not receiving treatment. Those in need of treatment include those subjects already with the undesired physiological change or disease as well as those subjects prone to have the physiological change or disease. An exemplary beneficial clinical outcome is to achieve remission for IBD, which may be assessed by clinical and visual examination of the G1 tract (e.g. by endoscopy).

The GM-CSF variants of the invention may also be administered to a subject to treat, prevent, and/or diagnose autoimmune pulmonary alveolar proteinosis (aPAP). aPAP is a rare lung disease resulting from the accumulation of surfactant protein. Surfactant homeostasis is normally maintained by alveolar macrophages in a GM-CSF-dependent manner (Tazawa, et al., (2014). *Chest,* 145(4), 729-737). The cause of aPAP has been attributed to high levels of GM-CSF autoantibodies in the lung which limit alveolar macrophage function. While whole lung lavage is the standard of care for aPAP, systemic or inhaled administration of GM-CSF has demonstrated clinical benefit to PAP patients (Seymour et al., (2001) *American Journal of Respiratory and Critical Care Medicine,* 163, 524-531).

Pharmaceutical Compositions and Administration

The invention also provides pharmaceutical compositions comprising the GM-CSF variants of the invention and a pharmaceutically acceptable carrier. For therapeutic use, the GM-CSF variants of the invention may be prepared as pharmaceutical compositions containing an effective amount of the antibody as an active ingredient in a pharmaceutically acceptable carrier. "Carrier" refers to a diluent, adjuvant, excipient, or vehicle with which the antibody of the invention is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine may be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the GM-CSF variants of the invention in such pharmaceutical formulation may vary, from less than about 0.5%, usually to at least about 1% to as much as 15 or 20% by weight and may be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, $21^{st}$ Edition, Troy, D. B. ed., Lipincott Williams and Wilkins, Philadelphia, Pa. 2006, Part 5, Pharmaceutical Manufacturing pp 691-1092, See especially pp. 958-989.

The mode of administration for therapeutic use of the GM-CSF variants of the invention may be any suitable route that delivers the variant to the host, such as parenteral administration, e.g., intradermal, intramuscular, intraperitoneal, intravenous or subcutaneous, pulmonary, transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

The GM-CSF variants of the invention may be administered to a subject by any suitable route, for example parentally by intravenous (i.v.) infusion or bolus injection, intramuscularly or subcutaneously or intraperitoneally. i.v. infusion may be given over for example 15, 30, 60, 90, 120, 180, or 240 minutes, or from 1, 2, 3, 4, 5, 6, 7, 8, 9, 10, 11 or 12 hours.

The dose given to a subject is sufficient to alleviate or at least partially arrest the disease being treated ("therapeutically effective amount") and may be sometimes 0.005 mg to about 100 mg/kg, e.g. about 0.05 mg to about 30 mg/kg or about 5 mg to about 25 mg/kg, or about 4 mg/kg, about 8 mg/kg, about 16 mg/kg or about 24 mg/kg, or for example about 1, 2, 3, 4, 5, 6, 7, 8, 9 or 10 mg/kg, but may even higher, for example about 15, 16, 17, 18, 19, 20, 21, 22, 23, 24, 25, 30, 40, 50, 60, 70, 80, 90 or 100 mg/kg.

A fixed unit dose may also be given, for example, 50, 100, 200, 500 or 1000 mg, or the dose may be based on the patient's surface area, e.g., 500, 400, 300, 250, 200, or 100 $mg/m^2$. Usually between 1 and 8 doses, (e.g., 1, 2, 3, 4, 5, 6, 7 or 8) may be administered to treat the patient, but 9, 10, 11, 12, 13, 14, 15, 16, 17, 18, 19, 20 or more doses may be given.

The administration of the GM-CSF variants of the invention may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose. For example, the GM-CSF variants of the invention may be administered at 8 mg/kg or at 16 mg/kg at weekly interval for 8 weeks, followed by administration at 8 mg/kg or at 16 mg/kg every two weeks for an additional 16 weeks, followed by administration at 8 mg/kg or at 16 mg/kg every four weeks by intravenous infusion.

For example, the GM-CSF variants of the invention may be provided as a daily dosage in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

The GM-CSF variants of the invention may also be administered prophylactically in order to reduce the risk of developing IBD, delay the onset of the occurrence of an event in IBD progression, and/or reduce the risk of recurrence when IBD is in remission.

The GM-CSF variants may be lyophilized for storage and reconstituted in a suitable carrier prior to use. This technique has been shown to be effective with conventional protein preparations and well known lyophilization and reconstitution techniques can be employed.

Oral Administration

The GM-CSF variants of the invention may be formulated for oral administration. The GM-CSF variants may be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized Additional agents can be included to facilitate absorption of the GM-CSF variant. Diluents, flavorings, low melting point waxes, vegetable oils, lubricants, suspending agents, tablet disintegrating agents, and binders may also be employed. Pharmaceutical compositions for oral administration can also be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally also include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

The GM-CSF variant pharmaceutical composition may be also provided in an enteric coating, the enteric coating being designed to protect and release the pharmaceutical composition in a controlled manner within the subject's lower gastrointestinal system, and to avoid systemic side effects. In addition to enteric coatings, the GM-CSF variants of the invention may be encapsulated, coated, engaged or otherwise associated within any compatible oral drug delivery system or component. For example, the GM-CSF variant of the invention may be provided in a lipid carrier system comprising at least one of polymeric hydrogels, nanoparticles, microspheres, micelles, and other lipid systems.

To overcome degradation in the small intestine, the GM-CSF variant of the invention may be contained within a hydrogel polymer carrier. The GM-CSF variant of the invention may be further formulated for compatible use with a carrier system that is designed to increase the dissolution kinetics and enhance intestinal absorption of the GM-CSF variant. For example, the GM-CSF variant may be formulated into liposomes, micelles and nanoparticles to increase GI tract permeation of the GM-CSF variants.

Various bioresponsive systems may also be combined with the GM-CSF variant of the invention to provide a pharmaceutical agent for oral delivery. In some embodiments, the GM-CSF variant is used in combination with a bioresponsive system, such as hydrogels and mucoadhesive polymers with hydrogen bonding groups (e.g., PEG, poly (methacrylic) acid [PMAA], cellulose, Eudragit®, chitosan and alginate) to provide a therapeutic agent for oral administration.

The GM-CSF variants of the invention may be administered in combination with permeation enhancers that promote the transport of the GM-CSF variants across the intestinal mucosa by increasing paracellular or transcellular permeation. Exemplary permeation enhancers comprise a long-chain fatty acid, a bile salt, an amphiphilic surfactant, and a chelating agent.

Combination Therapies

The invention also provides for a method of treating IBD, comprising administering to a subject in need thereof the GM-CSF variant of the invention in combination with a second therapeutic agent.

"In combination with" refers to administering of the GM-CSF variants of the invention described herein and a second therapeutic agent concurrently as single agents or sequentially as single agents in any order. In general, each agent will be administered at a dose and/or on a time schedule determined for that agent.

The second therapeutic agent may be any known therapy for IBD, including any agent or combination of agents that are known to be useful, or which have been used or are currently in use, for treatment of IBD. Such therapies and therapeutic agents include an aminosalicylates, a corticosteroid, an immunomodulator, an antibiotic, or a biologic.

Aminosalicylates are effective in treating mild to moderate cases of IBD as well as preventing relapses and maintaining remission. They are usually administered orally or rectally. Sulfasalazine (Azulfidine®), the first aminosalicylate to be widely used for IBD, is effective in achieving and maintaining remission in people with mild-to-moderate disease. It delivers 5-aminosalicylic acid (5-ASA) to the intestine but comes with disagreeable side effects in some patients, such as headache, nausea, loss of appetite, vomiting, rash, fever, and decreased white blood cell count. Sulfasalazine can decrease sperm production and function in men while they are taking the medication. It has been associated with pancreatitis in rare cases. The headaches, nausea, and rash are thought to be due to the release of the sulfapyridine moiety that is necessary for delivery of the 5-ASA to the intestine.

Other derivates of 5-ASA have also been synthesized. Those derivatives include Asacol® or Pentasa® (mesalamine), Dipentum® (olsalazine), and Colazal™ (balsalazide). Local mesalamine preparations bypass the stomach to avoid early digestion, and then release close to the inflamed section of the bowel. Oral, delayed-release preparations such as Pentasa® and Asacol® (mesalamine) can release 5-ASA directly to the small intestine and colon, or to the ileum and/or colon, respectively. Rowasa®, an enema formulation of mesalamine, allows the drug to be applied directly to the left colon. Rowasa® is effective in 80% of patients with mild-to-moderate colitis that affects only the left side of the colon. Mesalamine suppositories (Canasa®) that deliver the drug directly from the rectum up to the sigmoid colon are effective in a high proportion of patients with UC limited to the rectum and the lower end of the colon. Dipentum®, an oral, delayed-release preparation of olsalazine, delivers 5-ASA directly to the colon only.

As fast-acting anti-inflammatory and immunosuppressive agents, corticosteroids have been used for treating acute flare-ups of IBD for over 50 years. Since that time, these powerful agents have been the mainstay of treatment for disease. Most patients notice an improvement in symptoms within days of starting corticosteroids. This group of medications is available in oral, rectal, and intravenous (IV) forms. Corticosteroids are not effective in preventing flare-ups and therefore are rarely used for maintenance therapy in IBD. Since long-term use results in side effects, these agents are recommended only for short-term use in order to achieve remission, but they are not used frequently in the latter case. For people with moderate to severe active disease, oral corticosteroids include Deltasone® (prednisone), Medrol® (methylprednisolone), and hydrocortisone. Aminosalicylates are often taken together with corticosteroids.

Entocort® (budesonide), an oral corticosteroid, is used to treat mild-to-moderate Crohn's disease involving the end of the small intestine and/or the first part of the large intestine. This nonsystemic steroid targets the intestine rather than the whole body. Corticosteroids may also be given rectally as enemas (hydrocortisone, methylprednisone, Cortenema®), foams (hydrocortisone acetate, ProctoFoam-HC®), and suppositories. Such preparations are used for mild-to-moderate ulcerative colitis that is limited to the rectum or lower part of the colon. When used in combination with other therapies, these agents are also effective against more widespread disease that starts at the rectum. Methylprednisone and hydrocortisone are often given by IV infusion to patients with severe and extensive disease. Acute IBD does not respond to corticosteroid therapy in 20-30% of cases and in 30-40% of cases with moderate to severe disease, corticosteroids cannot be abruptly discontinued without occurrence of a disease flare-up.

Since IBD appears to be caused by an overactive immune system, immunomodulators play an important role in the treatment of this disease. These drugs are used for those who have one of the following characteristics: (a) side effects with corticosteroid treatment, (b) steroid-dependent disease, (c) do not respond to aminosalicylates, antibiotics, or corticosteroids, (d) perineal disease that does not respond to antibiotics, and (e) need to maintain remission. These drugs may be combined with a corticosteroid to speed up response during active flares of disease.

Imuran®, Azasan® (azathioprine) and Purinethol® (6-mercaptopurine, 6-MP) are oral immunomodulators that are used to maintain remission in Crohn's disease and UC. Since these agents have a slow onset of action, they are usually given along with another faster-acting drugs, e.g. corticosteroids. Other immunomodulators used for IBD are Sandimmune®, Neoral® (cyclosporine A) and Prograf® (tacrolimus). Of these agents, cyclosporine A has the fastest onset of action. When given IV at high doses, cyclosporine A is useful against active Crohn's disease. This drug is effective against severe UC as is tacrolimus. The latter agent can be used against Crohn's when corticosteroids are not effective or when fistulas develop. Tacrolimus may be applied topically to treat Crohn's disease of the mouth or perineal area. An option for people with Crohn's disease who do not respond to other treatments and cannot tolerate other immunosuppressants is IV-administered Rheumatrex® or Mexate® (methotrexate (MTX)).

Although no specific infectious agent has been identified as the cause of IBD, antibiotics are frequently used as a primary treatment. Antibiotics are effective as long-term therapy in Crohn's disease patients who have fistulas (between loops of intestine or between intestine and adjacent organs, e.g. skin) or recurrent abscesses near the anus. Patients whose active disease is successfully treated with antibiotics may be kept on these as maintenance therapy. Generally, antibiotics are not considered useful for those with UC; the exception is toxic megacolon.

The most frequently prescribed broad-spectrum antibiotics for IBD are Flagyl® (metronidazole) and Cipro® (ciprofloxacin). Metronidazole is a primary therapy for active Crohn's and has been shown to reduce the recurrence of Crohn's for the first three months after ileum resection surgery. This drug is effective in managing perineal Crohn's in over 50% of cases. Ciprofloxacin, much safer than metronidazole, is commonly used to treat active Crohn's disease. Both oral and IV metronidazole and ciprofloxacin are used for IBD treatment.

Possible targets by which biologics may interfere with the body's inflammatory response in IBD include tumor necrosis factor-alpha (TNF-$\alpha$), interleukins, adhesion molecules, colony-stimulating factors, and others. Since their mechanism is targeted, biologic therapies offer a distinct advantage in IBD treatment. Unlike corticosteroids, which tend to suppress the entire immune system and thereby produce major side effects, biologic agents act selectively. Biologics are targeted to particular enzymes and proteins that have already been proven defective, deficient, or excessive in people with IBD or in animal models of colitis. Anti-TNF agents have been used in both Crohn's disease and UC, such REMICADE® (infliximab), SIMPONI® (golimumab) and HUMIRA® (adalimumab).

Despite the above medication options for IBD, 66-75% of Crohn's patients and 25-40% of those with UC will eventually undergo surgery. Surgery for Crohn's disease depends upon the location of the disease. If it is in the small intestine, areas of diseased bowel may alternate with areas of normal bowel. The areas of active disease may narrow, forming strictures, which can block the passage of digested food. If the lesions are separated, strictureplasty is often used. Here, the strictured areas are widened and the small intestine is spared. Resection and anastomosis may be needed if the stricture is long or if there are multiple strictures close to each other. Although resection may offer years of relief, disease can recur at or near the site of the anastomosis. In patients with severe Crohn's in the colon, colectomy may be done. If the rectum is unaffected the end of the ileum may be rejoined to the rectum; thus, stool may be passed normally. If both the colon and rectum are involved, proctocolectomy with subsequent ileostomy may be performed. Fistulas and/or abscesses eventually develop in about 25% of patients with Crohn's disease. If fistulas are unresponsive to medication, they are removed by resection of the affected bowel followed by anastomosis. Abscesses must be drained; in some cases, this requires resection. For years, the standard surgery for UC has been proctocolectomy with ileostomy. Now the most common procedure is restorative proctocolectomy; this allows the patient to continue to pass stool through the anus. Unlike Crohn's disease, which can recur after surgery, UC is "cured" once the colon is removed.

Kits

One embodiment of the invention is a kit comprising the GM-CSF variant of the invention.

The kit may be used for therapeutic uses.

In some embodiments, the kit comprises the GM-CSF variant of the invention and reagents for detecting the GM-CSF variant. The kit can include one or more other elements including: instructions for use; other reagents, e.g., devices or other materials for preparing the GM-CSF variant for administration; pharmaceutically acceptable carriers; and devices or other materials for administration to a subject.

In some embodiments, the kit comprises the GM-CSF variant of the invention in a container.

In some embodiments, the kit comprises the GM-CSF variant of SEQ ID NO: 2.

In some embodiments, the kit comprises the GM-CSF variant of SEQ ID NO: 6.

In some embodiments, the kit comprises the GM-CSF variant of SEQ ID NO: 7.

In some embodiments, the kit comprises the GM-CSF variant of SEQ ID NO: 8.

In some embodiments, the kit comprises the GM-CSF variant of SEQ ID NO: 9.

The invention will now be described with specific, non-limiting examples.

Example 1: Materials and Methods

Production of Human GM-CSF Variants:

DNA and expression vectors encoding various $His_6$-tagged variants of GM-CSF were synthetically produced and used to transiently transfect Expi293 (HEK cells, Thermo-Scientific). The secreted protein was purified from cell supernatants by immobilized metal affinity chromatography and then buffer-exchanged into 1×PBS using standard methods and used for further characterization. Signal sequence used was MAWVWTLLFLMAAAQSIQA (SEQ ID NO: 19).

TF-1 Proliferation Assay $5\times10^3$ TF-1 cells (ATCC® CRL 2003™)/well were plated in 96-well plates (Costar 3603) in Assay Medium (RPMI1640—Gibco, 11875 containing 10% FBS—Gibco, 16140, 1% PenStrep—Gibco, 10378). Serial dilution of human GM-CSF variants as well as commercially-available recombinant protein (R&D Systems: Cat #215-GM/CF as a positive control) were prepared in Assay Medium and 50 μL/well of GM-CSF titrations was added to the cells. Cells were incubated for 72 h at 37° C. in a humidified incubator with a 5% $CO_2$ atmosphere. Cell proliferation was measured by the addition of Promega CellTiter 96® Aqueous One Solution (20 μL/well) according to manufacturer's protocol and incubating the cells for an additional 4 h at 37° C. The plates were shaken for 10 min at room temperature and the absorbance at 490 nm was read on a plate reader. Raw $OD_{490\ nm}$ values were plotted against the concentration of recombinant human GM-CSF (rhGM-CSF) using GraphPad Prism 6.02 to determine the $EC_{50}$ values.

Thermal Stability Analysis by Differential Scanning Calorimetry (DSC)

Differential scanning calorimetry was used to assess the thermal stability of the purified variants of GM-CSF. Briefly, purified protein was diluted to 1 mg/mL in 1×PBS and heated from 25-120° C. at a scan rate of 1° C./min using a MicroCal VP-DSC instrument. The calorimetric data was analyzed using Origin7 (Origin Lab Corporation). The raw calorimetric data was normalized to the sample concentration, baseline subtracted, and finally fit to a non-2-state model of unfolding using Origin7 software to obtain the $T_m$ value (temperature at the midpoint of unfolding) and other thermodynamic parameters.

Example 2: Design of GM-CSF Variants

GM-CSF variants were designed and subsequently characterized for their improved stability (conformational stability upon heating) while retaining and/or improving their ability to induce target cell proliferation.

Mutations were designed by the analysis of the human GM-CSF crystal structure, PDB code 2GMF (Rozwarski, Diederichs, Hecht, Boone, & Karplus, 1996). Positions for mutations were selected not to interfere with the receptor binding according to the crystal structure of the GM-CSF: receptor complex, PDB code 3CXE (Hansen et al., 2008). Additionally, the choice of L49P and R23L substitutions were supported by a consensus GM-CSF sequence generated from the alignment of primary amino acid sequences of the mature GM-CSF polypeptide from fifty different species. Consensus design for engineering thermostability in proteins has been described previously (M. Lehmann, Pasamontes, Lassen, & Wyss, 2000; M. Lehmann, Kostrewa, et al., 2000; Martin Lehmann & Wyss, 2001). FIG. 1 shows the crystal structure of the wild-type GM-CSF and the positions of the residues considered for substitution.

Table 5 shows the generated substitutions and the rationale for each substitution. Residue numbering is according to mature human GM-CSF of SEQ ID NO: 1. GM-CSF variants with the individual substitutions and combinations thereof were made and characterized for their cellular potency and stability using methods described in Example 1.

SEQ ID NO: 1
APARSPSPSTQPWEHVNAIQEARRLLNLSRDTAAEMNETVEVISEMFDLQ

EPTCLQTRLELYKQGLRGSLTKLKGPLTMMASHYKQHCPPTPETSCATQI

ITFESFKENLKDFLLVIPFDCWEPVQE cDNA encoding mature WT GM-CSF

SEQ ID NO: 18
GCCCCCGCCCGCTCCCCCTCCCCATCGACCCAACCCTGGGAACACGTGAA

CGCCATTCAGGAGGCTAGGAGACTGCTGAACCTGTCCCGGGATACCGCAG

CCGAGATGAACGAAACCGTGGAGGTCATCTCCGAAATGTTTGACTTGCAA

GAACCTACTTGTCTGCAAACTCGCCTCGAGCTGTACAAACAGGGACTCCG

GGGAAGCCTCACTAAGCTGAAGGGGCCTCTGACCATGATGGCCTCCCACT

ACAAGCAGCACTGCCCGCCGACGCCGGAAACCAGCTGCGCGACCCAGATC

ATTACCTTCGAATCGTTCAAGGAAAACCTGAAGGACTTCCTGCTTGTGAT

CCCGTTCGACTGCTGGGAGCCTGTGCAGGAGTAA

TABLE 5

| Substitution | Rationale |
|---|---|
| S29C/S69C | To create a novel disulfide bond that would link GM-CSF loop AB and loop BC. |
| L49P | Promote and stabilize the beta turn preceding helix B. |
| R23L | To create a leucine zipper interaction between helices A and D that would include adjacent residues I19, L26, L110 and L114 |
| K107I | To stabilize loop AB through hydrophobic interactions, specifically to improve interactions with adjacent residues L70 and F103. |

The R23L variant has been reported by Hercus et al. (Hercus et al., 1994) to have a two-fold increase in activity in the GM-CSF-dependent proliferation of primary CML cells. However, the substitution has not been linked to the resulting improved conformational stability.

The K107I substitution was included to stabilize loop AB through hydrophobic interactions with adjacent residues L70 and F103. There is precedent in nature for this combination of hydrophobic amino acids, L70/F103/I107, which are found in rat GM-CSF.

Table 6 shows the amino acid sequences of the generated variants and Table 7 shows the cDNA sequences encoding the generated GM-CSF variants. FIG. 2 shows the amino acid sequence alignments of the generated variants.

TABLE 6

| human GM-CSF Variant | SEQ ID NO: | Amino acid sequence |
|---|---|---|
| S29C/S69C | 2 | APARSPSPSTQPWEHVNAIQEARRLLNLCRDTAA<br>EMNETVEVISEMFDLQEPTCLQTRLELYKQGLRG<br>CLTKLKGPLTMMASHYKQHCPPTPETSCATQIIT<br>FESFKENLKDFLLVIPFDCWEPVQE |
| L49P | 3 | APARSPSPSTQPWEHVNAIQEARRLLNLSRDTAA<br>EMNETVEVISEMFDPQEPTCLQTRLELYKQGLRG<br>SLTKLKGPLTMMASHYKQHCPPTPETSCATQIIT<br>FESFKENLKDFLLVIPFDCWEPVQE |
| K107I | 4 | APARSPSPSTQPWEHVNAIQEARRLLNLSRDTAA<br>EMNETVEVISEMFDLQEPTCLQTRLELYKQGLRG<br>SLTKLKGPLTMMASHYKQHCPPTPETSCATQIIT<br>FESFIENLKDFLLVIPFDCWEPVQE |

TABLE 6-continued

| human GM-CSF Variant | SEQ ID NO: | Amino acid sequence |
|---|---|---|
| R23L | 5 | APARSPSPSTQPWEHVNAIQEALRLLNLSRDTAA<br>EMNETVEVISEMFDLQEPTCLQTRLELYKQGLRG<br>SLTKLKGPLTMMASHYKQHCPPTPETSCATQIIT<br>FESFKENLKDFLLVIPFDCWEPVQE |
| S29C/S69C/<br>L49P | 6 | APARSPSPSTQPWEHVNAIQEARRLLNLCRDTAA<br>EMNETVEVISEMFDPQEPTCLQTRLELYKQGLRG<br>CLTKLKGPLTMMASHYKQHCPPTPETSCATQIIT<br>FESFKENLKDFLLVIPFDCWEPVQE |
| S29C/S69C/<br>K107I | 7 | APARSPSPSTQPWEHVNAIQEARRLLNLCRDTAA<br>EMNETVEVISEMFDLQEPTCLQTRLELYKQGLRG<br>CLTKLKGPLTMMASHYKQHCPPTPETSCATQIIT<br>FESFIENLKDFLLVIPFDCWEPVQE |
| S29C/S69C/<br>R23L/L49P/<br>K107I | 8 | APARSPSPSTQPWEHVNAIQEALRLLNLCRDTAA<br>EMNETVEVISEMFDPQEPTCLQTRLELYKQGLRG<br>CLTKLKGPLTMMASHYKQHCPPTPETSCATQIIT<br>FESFIENLKDFLLVIPFDCWEPVQE |
| S29C/S69C/<br>L49P/K107I | 9 | APARSPSPSTQPWEHVNAIQEARRLLNLCRDTAA<br>EMNETVEVISEMFDPQEPTCLQTRLELYKQGLRG<br>CLTKLKGPLTMMASHYKQHCPPTPETSCATQIIT<br>FESFIENLKDFLLVIPFDCWEPVQE |

TABLE 7

| human GM-CSF Variant | SEQ ID NO: | cDNA sequence |
|---|---|---|
| S29C/S69C | 10 | GCCCCCGCCCGCTCCCCCTCCCCATCGACCCAAC<br>CCTGGGAACACGTGAACGCCATTCAGGAGGCTAG<br>GAGACTGCTGAACCTGTGCCGGGATACCGCAGCC<br>GAGATGAACGAAACCGTGGAGGTCATCTCCGAAA<br>TGTTTGACTTGCAAGAACCTACTTGTCTGCAAAC<br>TCGCCTCGAGCTGTACAAACAGGGACTCCGGGGA<br>TGTCTCACTAAGCTGAAGGGGCCTCTGACCATGA<br>TGGCCTCCCACTACAAGCAGCACTGCCCGCCGAC<br>GCCGGAAACCAGCTGCGCGACCCAGATCATTACC<br>TTCGAATCGTTCAAGGAAAACCTGAAGGACTTCC<br>TGCTTGTGATCCCGTTCGACTGCTGGGAGCCTGT<br>GCAGGAGTGATAA |
| L49P | 11 | GCCCCCGCCCGCTCCCCCTCCCCATCGACCCAAC<br>CCTGGGAACACGTGAACGCCATTCAGGAGGCTAG<br>GAGACTGCTGAACCTGTCCCGGGATACCGCAGCC<br>GAGATGAACGAAACCGTGGAGGTCATCTCCGAAA<br>TGTTTGACCCACAAGAACCTACTTGTCTGCAAAC<br>TCGCCTCGAGCTGTACAAACAGGGACTCCGGGGA<br>AGCCTCACTAAGCTGAAGGGGCCTCTGACCATGA<br>TGGCCTCCCACTACAAGCAGCACTGCCCGCCGAC<br>GCCGGAAACCAGCTGCGCGACCCAGATCATTACC<br>TTCGAATCGTTCAAGGAAAACCTGAAGGACTTCC<br>TGCTTGTGATCCCGTTCGACTGCTGGGAGCCTGT<br>GCAGGAGTGATAA |
| K107I | 12 | GCCCCCGCCCGCTCCCCCTCCCCATCGACCCAAC<br>CCTGGGAACACGTGAACGCCATTCAGGAGGCTAG<br>GAGACTGCTGAACCTGTCCCGGGATACCGCAGCC<br>GAGATGAACGAAACCGTGGAGGTCATCTCCGAAA<br>TGTTTGACTTGCAAGAACCTACTTGTCTGCAAAC<br>TCGCCTCGAGCTGTACAAACAGGGACTCCGGGGA<br>AGCCTCACTAAGCTGAAGGGGCCTCTGACCATGA<br>TGGCCTCCCACTACAAGCAGCACTGCCCGCCGAC<br>GCCGGAAACCAGCTGCGCGACCCAGATCATTACC<br>TTCGAATCGTTCATCGAAAACCTGAAGGACTTCC<br>TGCTTGTGATCCCGTTCGACTGCTGGGAGCCTGT<br>GCAGGAGTGATAA |
| R23L | 13 | GCCCCCGCCCGCTCCCCCTCCCCATCGACCCAAC<br>CCTGGGAACACGTGAACGCCATTCAGGAGGCTCT<br>TAGACTGCTGAACCTGTCCCGGGATACCGCAGCC |

TABLE 7-continued

| human GM-CSF Variant | SEQ ID NO: | cDNA sequence |
|---|---|---|
| | | GAGATGAACGAAACCGTGGAGGTCATCTCCGAAA<br>TGTTTGACTTGCAAGAACCTACTTGTCTGCAAAC<br>TCGCCTCGAGCTGTACAAACAGGGACTCCGGGGA<br>AGCCTCACTAAGCTGAAGGGGCCTCTGACCATGA<br>TGGCCTCCCACTACAAGCAGCACTGCCCGCCGAC<br>GCCGGAAACCAGCTGCGCGACCCAGATCATTACC<br>TTCGAATCGTTCAAGGAAAACCTGAAGGACTTCC<br>TGCTTGTGATCCCGTTCGACTGCTGGGAGCCTGT<br>GCAGGAGTGATAA |
| S29C/S69C/ L49P | 14 | GCCCCCGCCCGCTCCCCCTCCCCATCGACCCAAC<br>CCTGGGAACACGTGAACGCCATTCAGGAGGCTAG<br>GAGACTGCTGAACCTGTGCCGGGATACCGCAGCC<br>GAGATGAACGAAACCGTGGAGGTCATCTCCGAAA<br>TGTTTGACCCACAAGAACCTACTTGTCTGCAAAC<br>TCGCCTCGAGCTGTACAAACAGGGACTCCGGGGA<br>TGTCTCACTAAGCTGAAGGGGCCTCTGACCATGA<br>TGGCCTCCCACTACAAGCAGCACTGCCCGCCGAC<br>GCCGGAAACCAGCTGCGCGACCCAGATCATTACC<br>TTCGAATCGTTCAAGGAAAACCTGAAGGACTTCC<br>TGCTTGTGATCCCGTTCGACTGCTGGGAGCCTGT<br>GCAGGAGTGATAA |
| S29C/S69C/ K1071 | 15 | GCCCCCGCCCGCTCCCCCTCCCCATCGACCCAAC<br>CCTGGGAACACGTGAACGCCATTCAGGAGGCTAG<br>GAGACTGCTGAACCTGTGCCGGGATACCGCAGCC<br>GAGATGAACGAAACCGTGGAGGTCATCTCCGAAA<br>TGTTTGACTTGCAAGAACCTACTTGTCTGCAAAC<br>TCGCCTCGAGCTGTACAAACAGGGACTCCGGGGA<br>TGTCTCACTAAGCTGAAGGGGCCTCTGACCATGA<br>TGGCCTCCCACTACAAGCAGCACTGCCCGCCGAC<br>GCCGGAAACCAGCTGCGCGACCCAGATCATTACC<br>TTCGAATCGTTCATCGAAAACCTGAAGGACTTCC<br>TGCTTGTGATCCCGTTCGACTGCTGGGAGCCTGT<br>GCAGGAGTGATAA |
| S29C/S69C/ R23L/L49P/ K107I | 16 | GCCCCCGCCCGCTCCCCCTCCCCATCGACCCAAC<br>CCTGGGAACACGTGAACGCCATTCAGGAGGCTTT<br>GAGACTGCTGAACCTGTGCCGGGATACCGCAGCC<br>GAGATGAACGAAACCGTGGAGGTCATCTCCGAAA<br>TGTTTGACCCACAAGAACCTACTTGTCTGCAAAC<br>TCGCCTCGAGCTGTACAAACAGGGACTCCGGGGA<br>TGCCTCACTAAGCTGAAGGGGCCTCTGACCATGA<br>TGGCCTCCCACTACAAGCAGCACTGCCCGCCGAC<br>GCCGGAAACCAGCTGCGCGACCCAGATCATTACC<br>TTCGAATCGTTCATCGAAAACCTGAAGGACTTCC<br>TGCTTGTGATCCCGTTCGACTGCTGGGAGCCTGT<br>GCAGGAGTGATAA |
| S29C/S69C/ L49P/K107I | 17 | GCCCCCGCCCGCTCCCCCTCCCCATCGACCCAAC<br>CCTGGGAACACGTGAACGCCATTCAGGAGGCTAG<br>GAGACTGCTGAACCTGTGCCGGGATACCGCAGCC<br>GAGATGAACGAAACCGTGGAGGTCATCTCCGAAA<br>TGTTTGACCCACAAGAACCTACTTGTCTGCAAAC<br>TCGCCTCGAGCTGTACAAACAGGGACTCCGGGGA<br>TGTCTCACTAAGCTGAAGGGGCCTCTGACCATGA<br>TGGCCTCCCACTACAAGCAGCACTGCCCGCCGAC<br>GCCGGAAACCAGCTGCGCGACCCAGATCATTACC<br>TTCGAATCGTTCATCGAAAACCTGAAGGACTTCC<br>TGCTTGTGATCCCGTTCGACTGCTGGGAGCCTGT<br>GCAGGAGTGATAA |

Table 8 shows the summary of thermal stability of human GM-CSF variants, measured using methods described in Example 1 and expressed as the melting temperature $T_m$ and shift in the $T_m$ when compared to the wild-type GM-CSF protein. All variants exhibited significantly improved thermal stability when compared to the wild-type protein. From the individual substitutions, introduction of the disulfide bridge in the S29C/S69C into the wild-type GM-CSF resulted in the most enhanced stabilization when compared to the L49P, K107Iand R23L substitutions alone. Introduction of variants combinatorially further improved the thermal stability of the resulting variant in an approximately additive manner. The variant containing all five amino acid substitutions described above, S29C/S69C/R23L/L49P/K107I, had a $T_m$ value that was more than 28° C. greater than that of the wild-type protein.

TABLE 8

| Protein | Thermal stability | |
|---|---|---|
| | $T_m$ (° C.) | $\Delta T_m$ (° C.)* |
| Wild type | 67.06 | 0.00 |
| S29C/S69C | 80.86 | 13.80 |
| L49P | 73.84 | 6.78 |
| K107I | 73.95 | 6.89 |
| R23L | 71.64 | 4.58 |
| S29C/S69C/L49P | 87.47 | 20.41 |
| S29C/S69C/K107I | 86.09 | 19.03 |
| S29C/S69C/R23L/L49P/K107I | 95.27 | 28.21 |
| S29C/S69C/L49P/K107I | 92.49 | 25.43 |

*relative to the wild type protein

The resulting variants were tested for their potency in a TF-1 cell proliferation assay. Table 9 shows the $EC_{50}$ values for each variant expressed as mean of two individual measurements and the fold change when compared to the wild-type GM-CSF. The S29C/S69C demonstrated about 2.6-fold improvement when compared to the wild-type GM-CSF. The individual substitutions L49P and R23L had a modest improvement in potency whereas the K107I substitution resulted in a variant with slightly reduced potency. Generally, increases in the cellular potency of the GM-CSF variants correlated with the conformation stability of the variants with the most stable variant (S29C/S69C/R23L/L49P/K107I) exhibiting the greatest enhancement (4-fold) in stimulating the proliferation of TF-1 cells.

TABLE 9

| Protein | $EC_{50}$ (pM) | Fold-$EC_{50}$ change* |
|---|---|---|
| Wild-type GM-CSF | 13.095 | 1.00 |
| S29C/S69C | 5.0235 | 2.61 |
| L49P | 12.54 | 1.04 |
| K107I | 24.535 | 0.53 |
| R23L | 11.848 | 1.11 |
| S29C/S69C/L49P | 10.141 | 1.29 |
| S29C/S69C/K107I | 3.8145 | 3.43 |
| S29C/S69C/R23L/L49P/K107I | 3.618 | 3.62 |
| S29C/S69C/L49P/K107I | 8.514 | 1.54 |

*Relative to the wild-type GM-CSF

Example 3: GM-CSF Variants are Stabile in Fasted State Simulated Intestinal Fluid Orally-administered GM-CSF for local delivery could prove more desirable from a patient compliance as well as from a safety perspective by minimizing systemic exposure. However, the oral delivery of protein to the lower gastrointestinal tract presents numerous challenges owing to the harsh pH, proteolytic, and microbial environments to which the biologic drug would be exposed (Amidon, Brown, & Dave, 2015).

Stability of the generated GM-CSF variants were tested in fasted state simulated intestinal fluids (FaSSIF) supplemented with pancreatin (3 mg/mL; trypsin, amylase, lipase, ribonuclease, and other proteases) in order to assess their stability in an environment comparable to portions of the GI tract.

FaSSIF-V2 (Biorelevant; London, UK) was prepared fresh according to the manufacturer's specifications and supplemented with pancreatin from porcine pancreas (Sigma; St. Louis, Mo., USA) at a final concentration of 3 mg/mL. GM-CSF variants formulated in 1×PBS were diluted to a final concentration of 1 mg/mL with FaSSIF (containing pancreatin) and incubated at 37° C. for 0-30 min. The digestion was arrested by heating the samples at 95° C. for 5 min followed by freezing. SDS-PAGE analysis of the samples was performed by loading 10 μg of GM-CSF (based on pre-treatment concentration) per lane. The resulting gel was analyzed by densitometry to quantitate the amount of intact variant GM-CSF remaining, which was expressed as a percentage of the untreated control.

Figure 3:
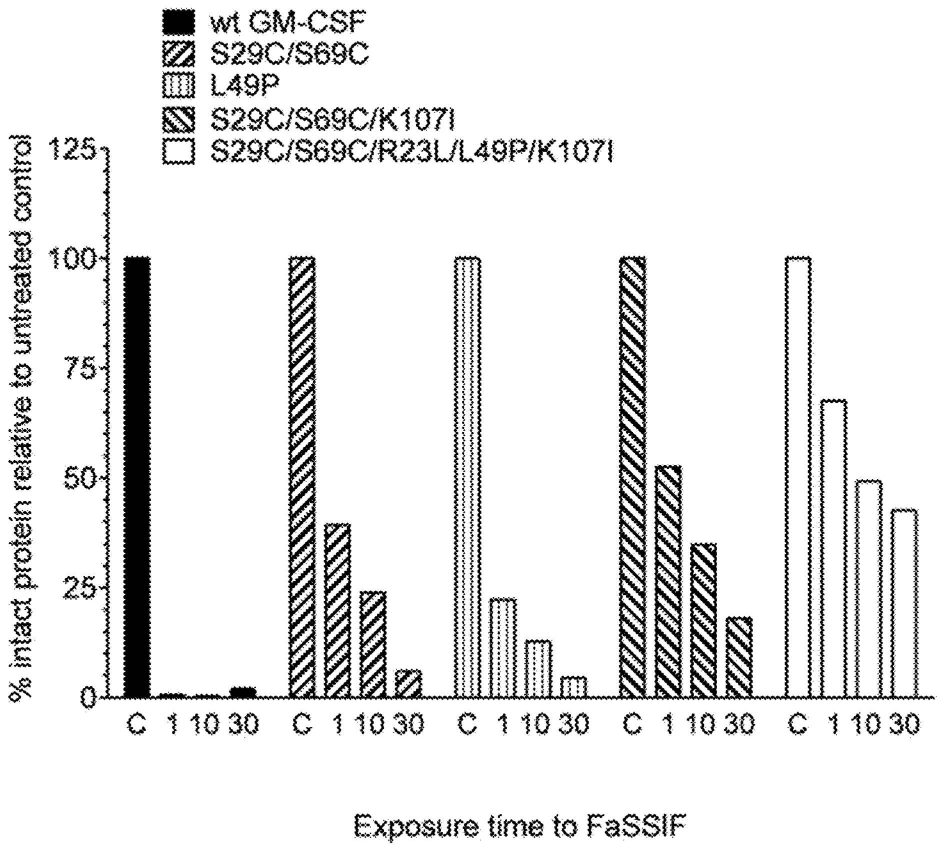
FIG. 3 shows the stability of S29C/S69C, L49P, S29C/S69C/K107I and S29C/S69C/R23L/L49P/K107IGM-CSF variants over time (1, 10 and 30 minutes as indicated in the Figure) in fasted state simulated intestinal fluid (FaSSIF) with 3 mg/mL pancreatin. C: control.

All tested variants except the R23L variant (data not shown) demonstrated improved stability to proteolytic degradation over time when compared to the wild type GM-CSF. FIG. 3 shows the stability of S29C/S69C, L49L, S29C/S69C/K107I and S29C/S69C/R23L/L49P/K107I GM-CSF variants over time in FaSSIF containing 3 mg/mL pancreatin. Compared to the wild type GM-CSF which is completely degraded in less than one minute in FaSSIF containing pancreatin, more than half of the S29C/S69C/R23L/L49P/K107I variant protein remains intact after 30 minutes of enzymatic exposure.

Example 4: In Silico Assessment of Immunogenicity Risk of Select GM-CSF Variants Two GM-CSF variants were subjected to in silico analysis to determine if any of the amino acid substitutions (relative to wild-type GM-CSF) would be predicted to increase the binding affinity of any 9-mer peptides to class II MHC molecules and therefore predict T cell epitopes using ImmunoFilter™ Technology. No major potential immunogeneicity liabilities were identified in the variants tested (S29C/S69C/R23L/L49P/K107I and S29C/S69C/L49P/K107I variants).

The L49P amino acid substitution appeared to reduce the immunogenicity risk. The predicted binding scores of one 9-mer with the L49P substitution to HLA-DR1, HLA-DR3, HLA-DR4 and HLA-DR5 was reduced from 24-32% to 4-8%.

Example 5: GM-CSF Variants Retain their Functional Activity in Fasted State Simulated Intestinal Fluid (FaSSIF)

Biological activity of GM-CSF variants R23L/S29C/L49P/S69C/K107I and S29C/L49P/S69C/K107I was assessed after exposure to FaSSIF supplemented with trypsin, amylase and lipase, ribonuclease, and other proteases, produced by exocrine cells of the porcine pancreas proteases and ribonucleases at various time periods as indicated below and in FIG. 4A, FIG. 4B, FIG. 4C and FIG. 4D.

Figure 4A:
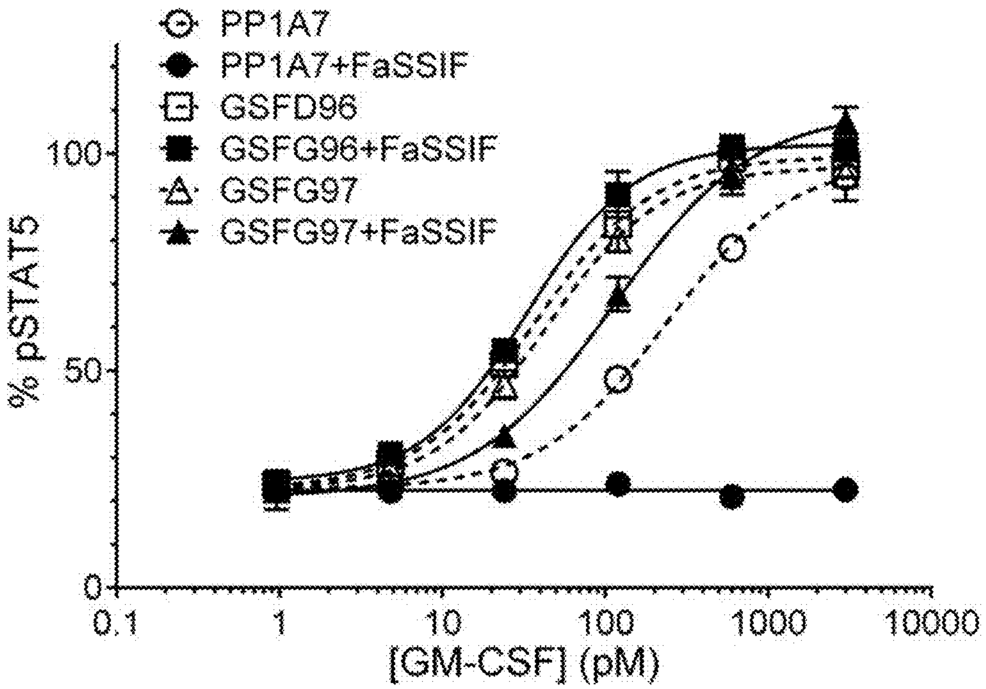
FIG. 4A shows that biological activity of the GM-CSF variants R23L/S29C/L49P/S69C/K107I and S29C/L49P/S69C/K107Iwas retained after 30 minute incubation with FaSSIF supplemented with 3 mg/mL pancreatin, whereas the biological activity of the wild-type GM-CSF was completely abrogated. PP1A7: wild-type GM-CSF, GSFD96: R23L/S29C/L49P/S69C/K107Ivariant; GSFD97: S29C/L49P/S69C/K107I variant. Biological activity was measured in TF-1 cells by assessing percent (%) phosphorylation of Tyr694 of STAT5 and plotted as a function of GM-CSF concentration used in the assays.
Figure 4B:
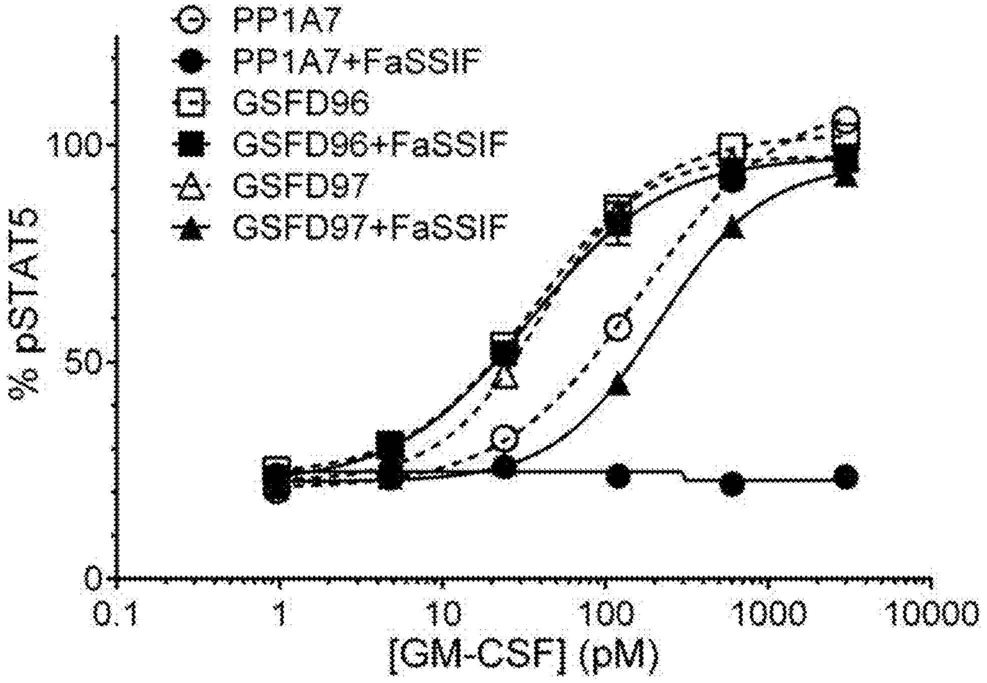
FIG. 4B shows that biological activity of the GM-CSF variants R23L/S29C/L49P/S69C/K107I and S29C/L49P/S69C/K107I was retained after 1 hour of incubation with FaSSIF supplemented with 3 mg/mL pancreatin at comparable levels to that of the wild-type GM-CSF without FaSSIF+pancreatin. PP1A7: wild-type GM-CSF, GSFD96: R23L/S29C/L49P/S69C/K107I variant; GSFD97: S29C/L49P/S69C/K107I variant. Biological activity was measured in TF-1 cells by assessing percent (%) phosphorylation of Tyr694 of STAT5 and plotted as a function of GM-CSF concentration used in the assays.
Figure 4C:
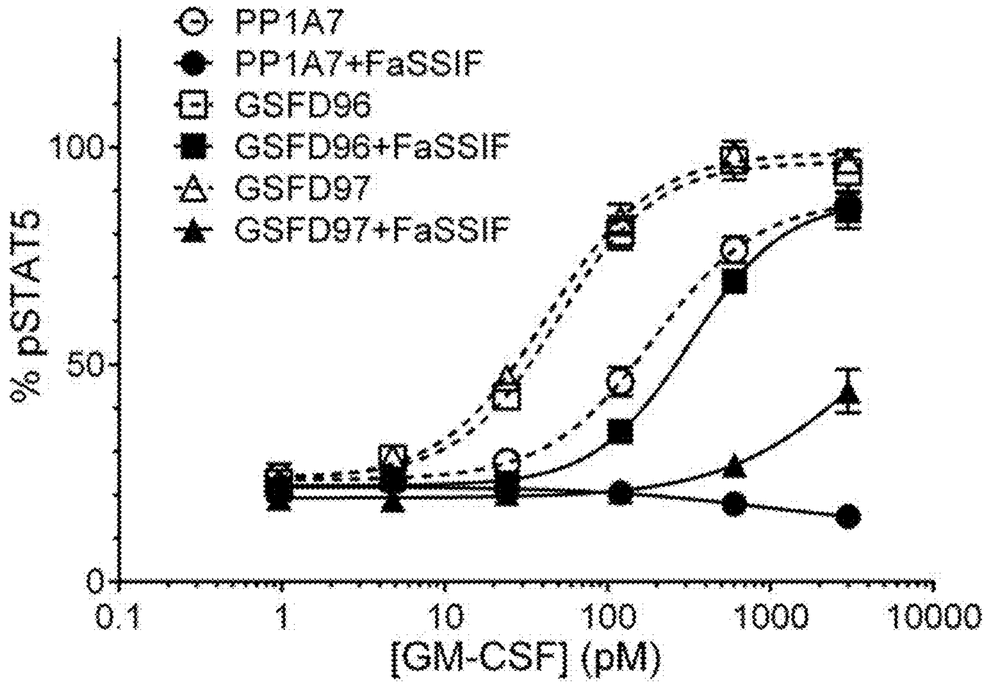
FIG. 4C shows that biological activity of the GM-CSF variant R23L/S29C/L49P/S69C/K107I was retained after 4 hours of incubation with FaSSIF supplemented with 3 mg/mL pancreatin at comparable levels to that of the wild-type GM-CSF without FaSSIF+pancreatin and that the variant S29C/L49P/S69C/K107I demonstrates some activity at this time point. PP1A7: wild-type GM-CSF, GSFD96: R23L/S29C/L49P/S69C/K107I variant; GSFD97: S29C/L49P/S69C/K107I variant. Biological activity was measured in TF-1 cells by assessing percent (%) phosphorylation of Tyr694 of STAT5 and plotted as a function of GM-CSF concentration used in the assays.
Figure 4D:
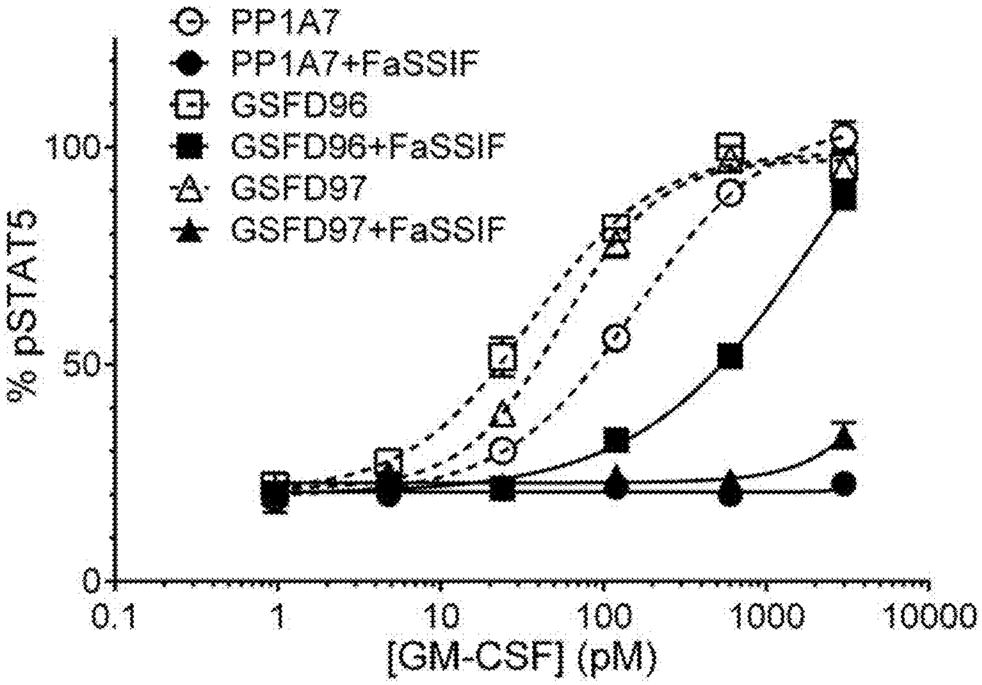
FIG. 4D shows that biological activity of the GM-CSF variant R23L/S29C/L49P/S69C/K107I was retained after 6 hours of incubation with FaSSIF supplemented with 3 mg/mL pancreatin. PP1A7: wild-type GM-CSF, GSFD96: R23L/S29C/L49P/S69C/K107I variant; GSFD97: S29C/L49P/S69C/K107I variant. Biological activity was measured in TF-1 cells by assessing percent (%) phosphorylation of Tyr694 of STAT5 and plotted as a function of GM-CSF concentration used in the assays.

Both variants R23L/S29C/L49P/S69C/K107I and S29C/L49P/S69C/K107I retained their activity completely or partially at 30 minutes (FIG. 4A), 1 hour (FIG. 4B) and 4 hours (FIG. 4C) of exposure to the proteolytic environment mimicking the GI tract, whereas the wild-type GM-CSF was completely inactive after 30 minutes of exposure (FIG. 4A). The variant R23L/S29C/L49P/S69C/K107I retained a substantial portion of its biological activity even after 6 hours of exposure to the proteolytic environment (FIG. 4D). Both variants were more potent in inducing STAT5 phosphorylation when compared to the wild-type GM-CSF even in non-proteolytic environment (incubation in the absence of FaSSIF).

Methods

Variants of human GM-CSF were diluted to a final concentration of 1 mg/mL in simulated intestinal fluid (prepared from FaSSIF-v2 powder; Biorelevant; London, UK), which was supplemented with porcine pancreatin (Sigma; St. Louis, Mo.) at a final concentration of 3 mg/mL. Variants of human GM-CSF were incubated in this solution at 37° C. for 0.5-6 hours. Proteolytic digestion was arrested by the addition of complete protease inhibitor (Roche) to 10×. Simulated intestinal fluid-treated GM-CSF samples were serially diluted twofold in RPMI1640 serum-free media (Gibco) and applied to TF-1 cells (ATCC; 1e5 cells/well), which had been serum starved for 2 hours at 37° C. with 5% $CO_2$. Treated TF-1 cells were incubated for 15 min at 37° C. The TF-1 cells were collected by centrifugation and lysed with Tris lysis buffer containing protease and phosphatase inhibitors (Meso Scale Discovery). Phosphorylation of STAT5 (Tyr694) relative to total STAT5a,b was determined by immunoassay (Meso Scale Discovery). Phosphorylation of STAT5 protein (% relative to total STAT5a,b) was plotted as a function of GM-CSF concentration.

Example 6: GM-CSF Variants Retain their Functional Activity Upon Exposure to Colon Content Biological activity of GM-CSF variants R23L/S29C/L49P/S69C/K107I and S29C/L49P/S69C/K107I was assessed after exposure to colon content from naïve cynomolgus monkeys at various time periods.

Figure 5A:
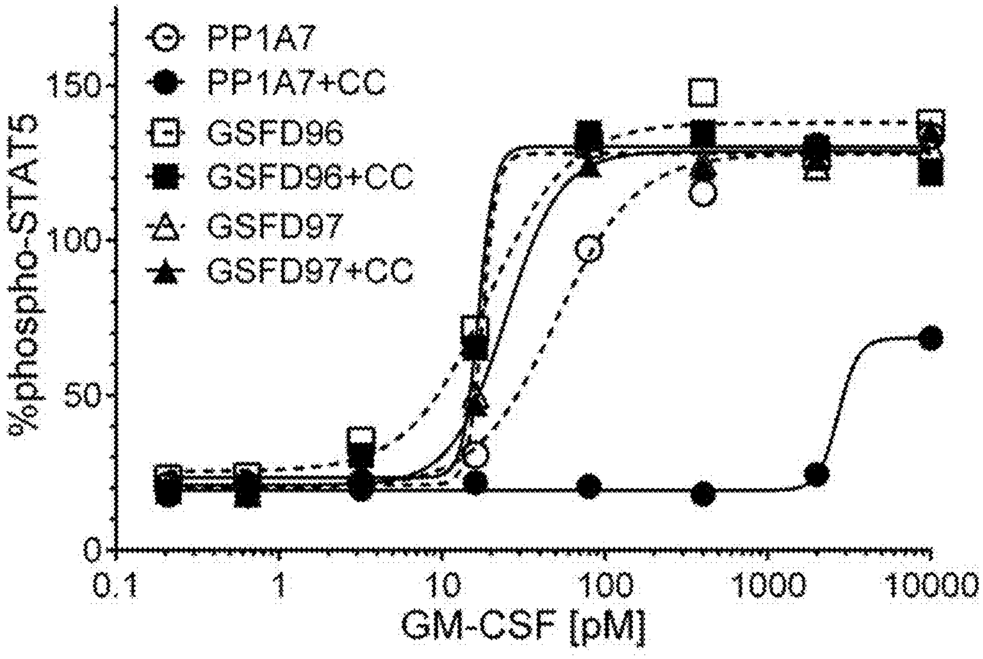
FIG. 5A shows that biological activity of the GM-CSF variants R23L/S29C/L49P/S69C/K107I and S29C/L49P/S69C/K107I was retained after incubation for 30 minutes with colon content from naïve cynomolgus monkeys (CC), whereas the biological activity of the wild-type GM-CSF was almost completely abolished. PP1A7: wild-type GM-CSF, GSFD96: R23L/S29C/L49P/S69C/K107I variant; GSFD97: S29C/L49P/S69C/K107I variant. Biological activity was measured in TF-1 cells by assessing percent (%) phosphorylation of Tyr694 of STAT5 and plotted as a function of GM-CSF concentration used in the assays.

FIG. 5A shows that biological activity of the GM-CSF variants R23L/S29C/L49P/S69C/K107I and S29C/L49P/S69C/K107I was fully retained after incubation for 30 minutes with colon content from naïve cynomolgus monkeys, whereas the biological activity of the wild-type GM-CSF was almost completely abolished.

Figure 5B:
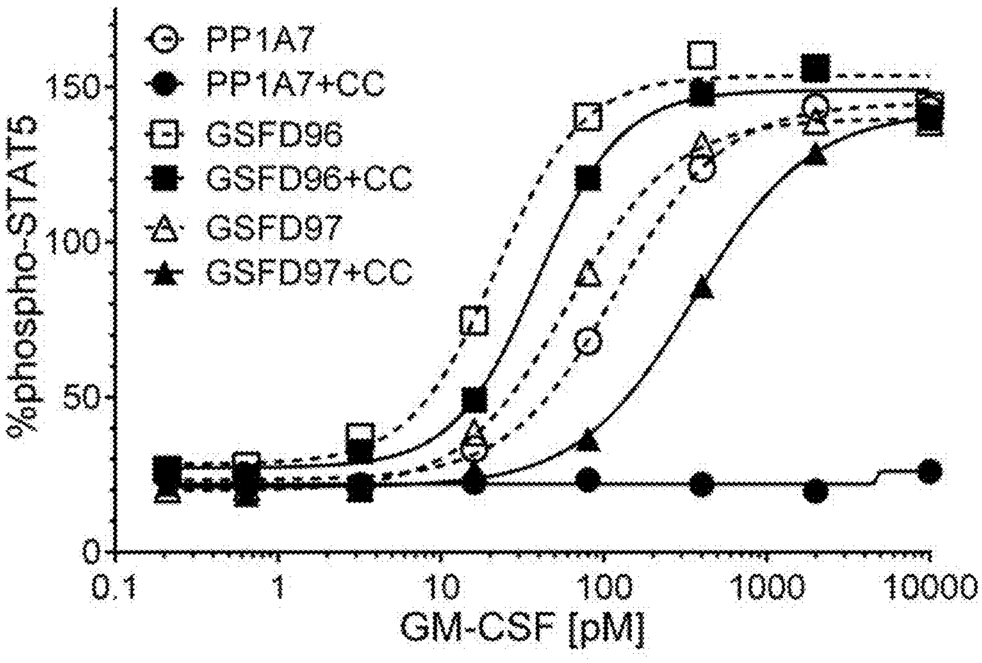
FIG. 5B shows that biological activity of the GM-CSF variants R23L/S29C/L49P/S69C/K107I and S29C/L49P/S69C/K107I was retained after incubation for 2 hours with colon content from naïve cynomolgus monkeys (CC). PP1A7: wild-type GM-CSF, GSFD96: R23L/S29C/L49P/S69C/K107I variant; GSFD97: S29C/L49P/S69C/K107I variant. Biological activity was measured in TF-1 cells by assessing percent (%) phosphorylation of Tyr694 of STAT5 and plotted as a function of GM-CSF concentration used in the assays.

FIG. 5B shows that biological activity of the GM-CSF variants R23L/S29C/L49P/S69C/K107I and S29C/L49P/S69C/K107I was retained after incubation for 2 hours with colon content from naïve cynomolgus monkeys. The R23L/S29C/L49P/S69C/K107I variant of GM-CSF exhibited only a twofold loss in activity after exposure to colon content for two hours and still possessed potency that was twofold greater than wild-type GM-CSF that was not exposed to colon content. The S29C/L49P/S69C/K107I variant of GM-CSF exhibited a 6-fold loss of activity compared to the untreated cytokine.

Figure 5C:
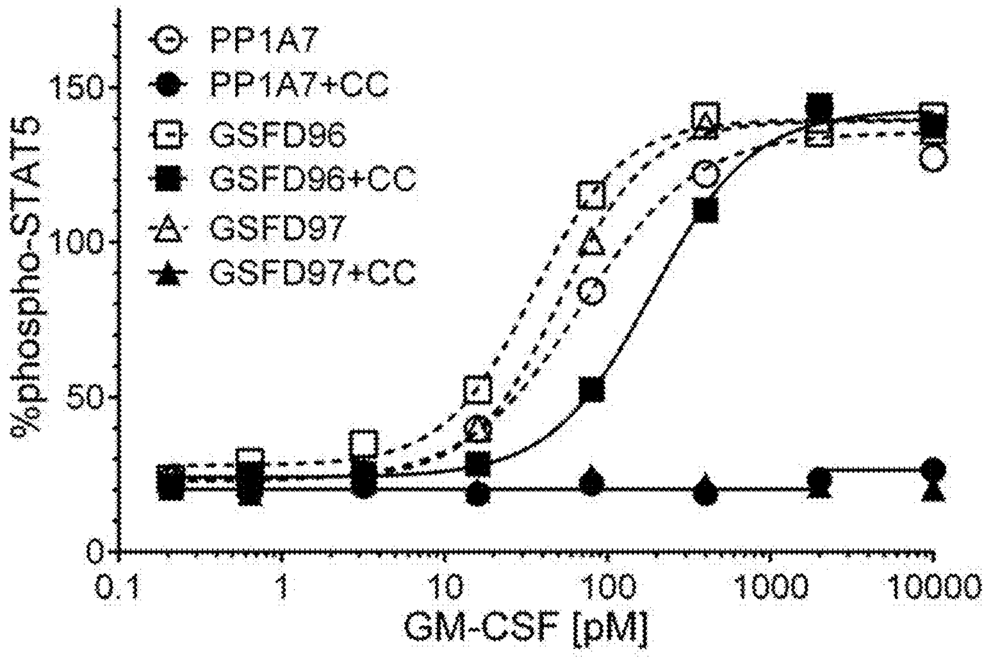
FIG. 5C shows that biological activity of the GM-CSF variant R23L/S29C/L49P/S69C/K107I was retained after incubation for 6 hours with colon content from naïve cynomolgus monkeys (CC). The R23L/S29C/L49P/S69C/K107I variant of GM-CSF exhibited a 5-fold loss of activity compared to the untreated variant cytokine while the activity of wild-type GM-CSF was completely abolished. PP1A7: wild-type GM-CSF, GSFD96: R23L/S29C/L49P/S69C/K107I variant; GSFD97: S29C/L49P/S69C/K107I variant. Biological activity was measured in TF-1 cells by assessing percent (%) phosphorylation of Tyr694 of STAT5 and plotted as a function of GM-CSF concentration used in the assays.

FIG. 5C that shows that biological activity of the GM-CSF variant R23L/S29C/L49P/S69C/K107I was retained after incubation for 6 hours with colon content from naïve cynomolgus monkeys. The R23L/S29C/L49P/S69C/K107I variant of GM-CSF exhibited a 5-fold loss of activity compared to the untreated variant cytokine while the activity of wild-type GM-CSF was completely abolished.

Figure 5D:
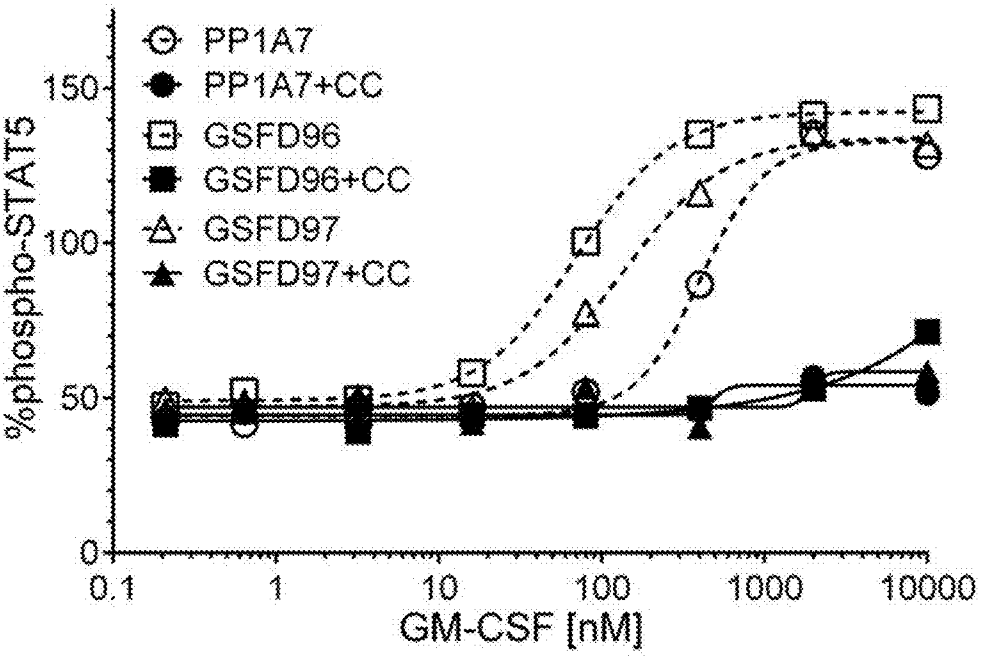
FIG. 5D shows that biological activity of GM-CSF and its variants S29C/L49P/S69C/K107I and R23L/S29C/L49P/S69C/K107I was abolished after incubation for 24 hours with colon content from naïve cynomolgus monkeys (CC). PP1A7: wild-type GM-CSF, GSFD96: R23L/S29C/L49P/S69C/K107I variant; GSFD97: S29C/L49P/S69C/K107I variant. Biological activity was measured in TF-1 cells by assessing percent (%) phosphorylation of Tyr694 of STAT5 and plotted as a function of GM-CSF concentration used in the assays.

FIG. 5D shows that biological activity of GM-CSF and its variants S29C/L49P/S69C/K107I and R23L/S29C/L49P/S69C/K107I was abolished after incubation for 24 hours with colon content from naïve cynomolgus monkeys.

Table 10 shows the $EC_{50}$ values in the functional assay for the variants.

TABLE 10

| Incubation time Colon content | EC$_{50}$ (pM) | | | | | |
|---|---|---|---|---|---|---|
| | WT GM-CSF | | S29C/L49P/ S69C/K107I variant | | R23L/S29C/L49P/ S69C/K107I variant | |
| | − | + | − | + | − | + |
| 0.5 hrs | 50 | 2,700 | 18 | 25 | 19 | 17 |
| 2 hrs | 120 | ND | 60 | 360 | 22 | 39 |
| 6 hrs | 69 | ND | 51 | ND | 35 | 190 |
| 24 hrs | 410 | ND | 135 | ND | 70 | ND |

ND = No activity detected;
WT: wild-type

Materials and Methods

Variants of human GM-CSF were diluted to a final concentration of 1 mg/mL in either 1× phosphate-buffered saline or colon content from naïve cynomolgus monkeys (BioreclamationIVT; Long Island, N.Y.), which was normalized to a final protein concentration of 3 mg/mL in 1× phosphate-buffered saline. Variants of human GM-CSF were incubated in this solution at 37° C. for 0.5-24 hours. After the indicated incubation period, GM-CSF containing samples were serially diluted twofold in RPMI1640 serum-free media (Gibco) and applied to TF-1 cells (ATCC; 1e5 cells/well), which had been serum starved for 2 hours at 37° C. with 5% $CO_2$. Treated TF-1 cells were incubated for 15 min at 37° C. The TF-1 cells were collected by centrifugation and lysed with Tri lysis buffer (Meso Scale Discovery; Rockville, Md.) containing protease and phosphatase inhibitors (Roche Life Science). Phosphorylation of STAT5 (Tyr694) relative to total STAT5a,b was determined by immunoassay (Meso Scale Discovery). Phosphorylation of STAT5 (% relative to total STAT5a,b) was plotted as a function of GM-CSF concentration. In the experiments, wild-type GM-CSF and S29C/L49P/S69C/K107I variant had a 6×-His tag at the C-terminus coupled to GM-CSF via a GS linker.

Example 7: GM-CSF Variants Retain their Functional Activity in Different Canine Simulated Small Intestinal Fluid (SSIF)

The ability of wild-type human GM-CSF and GM-CSF variant R23L/S29C/L49P/S69C/K107I to stimulate STAT5 phosphorylation in TF-1 cells was assessed after a two-hour exposure to SSIF supplemented with trypsin, amylase and lipase, ribonuclease, and other proteases, produced by exocrine cells of the porcine pancreas proteases and ribonucleases as indicated in Table 11.

The functional activity of His-tagged wild-type human GM-CSF was completely abolished following a two-hour exposure to any of the four preparations of canine SSIF. Variant R23L/S29C/L49P/S69C/K107I retained complete stimulatory activity after a two-hour exposure when SSIF was prepared at pH 7 and supplemented with 1 mg/mL pancreatin, which is equivalent to 200 USP units of protease activity per milliliter. When exposed to ten times more pancreatin (10 mg/mL; 2,000 USP units/mL) at pH 7.0 over the same timeframe, R23L/S29C/L49P/S69C/K107I GM-CSF exhibited a 24-fold loss in potency relative to variant GM-CSF not exposed to SSIF. Variant R23L/S29C/L49P/S69C/K107I exhibited a 5-fold loss in functional activity after a two-hour exposure to canine SSIF when the simulated fluid was prepared at pH 5.5 and supplemented with 1 mg/mL pancreatin, which is equivalent to 200 USP units of protease activity per milliliter. When exposed to ten times more pancreatin (10 mg/mL; 2,000 USP units/mL) at pH 5.5, R23L/S29C/L49P/S69C/K107I GM-CSF exhibited a 47-fold loss in potency relative to the non-pretreated sample. Even in the absence of pre-treatment with canine SSIF, R23L/S29C/L49P/S69C/K107I GM-CSF was two and a half times more potent than wild-type GM-CSF at inducing STAT5 phosphorylation in TF-1 cells.

TABLE 11

| [Pancreatin] (mg/mL) | pH | EC$_{50}$ value (pM) | |
|---|---|---|---|
| | | WT GM-CSF | S29C/S69C/R23L/L49P/K107I variant |
| 10 | 5.5 | No Activity | 166 |
| 10 | 7.0 | No Activity | 85.2 |
| 1 | 5.5 | No Activity | 16.4 |
| 1 | 7.0 | No Activity | 2.94 |
| 0 (control) | 7.2 | 8.68 | 3.55 |

Methods

Variants of human GM-CSF were diluted to a final concentration of 1 mg/mL in simulated intestinal fluid (prepared from Dog FaSSIF/Dog FaSSGF powder at a final pH of either 5.5 or 7; Biorelevant; London, UK), which was supplemented with porcine pancreatin (Sigma Catalog P7545; St. Louis, Mo.) at a final concentration of either 1 or 10 mg/mL. Variants of human GM-CSF were incubated in this solution at 37° C. for 2 hours. Proteolytic digestion was arrested by the addition of complete protease inhibitor (Roche) to 10×. Simulated intestinal fluid-treated GM-CSF samples were serially diluted twofold in RPMI1640 serum-free media (Gibco) and applied to TF-1 cells (ATCC; 1e5 cells/well), which had been serum starved for 2 hours at 37° C. with 5% $CO_2$. Treated TF-1 cells were incubated for 15 min at 37° C. The TF-1 cells were collected by centrifugation and lysed with Tris lysis buffer containing protease and phosphatase inhibitors (Meso Scale Discovery). Phosphorylation of STAT5 (Tyr694) relative to total STAT5a,b was determined by immunoassay (Meso Scale Discovery). Phosphorylation of STAT5 protein (% relative to total STAT5a,b) was plotted as a function of GM-CSF concentration. Curve-fitting was performed in Prism 7 (GraphPad) to obtain the EC$_{50}$ values.

We claim:

1. An isolated GM-CSF variant comprising an amino acid sequence of SEQ ID NO: 8.

2. The GM-CSF variant of claim 1, wherein the variant is conjugated to a half-life extending moiety.

3. The GM-CSF variant of claim 2, wherein the half-life extending moiety is a human serum albumin (HSA) or variant thereof, an antibody Fc region or fragment thereof, an albumin-binding domain or a polyethylene glycol.

4. The GM-CSF variant of claim 2, wherein the half-life extending moiety is conjugated to the GM-CSF variant via a linker.

5. The GM-CSF variant of claim 4, wherein the linker comprises the amino acid sequence of SEQ ID NOs: 20, 21, 22, 23, 24, 25, 26, 27, 28, 29 or 30.

6. A pharmaceutical composition comprising the GM-CSF variant of claim 1 and a pharmaceutically acceptable excipient.

* * * * *

SEQUENCE LISTING

```
<160> NUMBER OF SEQ ID NOS: 33

<210> SEQ ID NO 1
<211> LENGTH: 127
<212> TYPE: PRT
<213> ORGANISM: Homo sapiens

<400> SEQUENCE: 1
```

```
Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125


<210> SEQ ID NO 2
<211> LENGTH: 127
<212> TYPE: PRT
<213> ORGANISM: Artificial Sequence
<220> FEATURE:
<223> OTHER INFORMATION: S29C/S69C GM-CSF variant

<400> SEQUENCE: 2

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Cys Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Cys Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125


<210> SEQ ID NO 3
<211> LENGTH: 127
<212> TYPE: PRT
<213> ORGANISM: Artificial Sequence
<220> FEATURE:
<223> OTHER INFORMATION: L49P  GM-CSF variant

<400> SEQUENCE: 3

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Pro Gln Glu Pro Thr Cys Leu Gln Thr Arg Leu Glu Leu Tyr Lys Gln
```

-continued

```
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125


<210> SEQ ID NO 4
<211> LENGTH: 127
<212> TYPE: PRT
<213> ORGANISM: Artificial Sequence
<220> FEATURE:
<223> OTHER INFORMATION: K107I variant

<400> SEQUENCE: 4

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Ile Glu Asn Leu Lys Asp
            100                 105                 110

Phe Leu Leu Val Ile Pro Phe Asp Cys Trp Glu Pro Val Gln Glu
        115                 120                 125


<210> SEQ ID NO 5
<211> LENGTH: 127
<212> TYPE: PRT
<213> ORGANISM: Artificial Sequence
<220> FEATURE:
<223> OTHER INFORMATION: R23L  GM-CSF variant

<400> SEQUENCE: 5

Ala Pro Ala Arg Ser Pro Ser Pro Ser Thr Gln Pro Trp Glu His Val
1               5                   10                  15

Asn Ala Ile Gln Glu Ala Leu Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110
```

```
Phe Leu Leu Val Ile Pro Phe Asp Cys Trp Glu Pro Val Gln Glu
        115                 120                 125


<210> SEQ ID NO 6
<211> LENGTH: 127
<212> TYPE: PRT
<213> ORGANISM: Artificial Sequence
<220> FEATURE:
<223> OTHER INFORMATION: S29C/S69C/L49P  GM-CSF variant

<400> SEQUENCE: 6

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Cys Arg Asp Thr
            20                  25                  30

Ala Ala Glu Met Asn Glu Thr Val Glu Val Ile Ser Glu Met Phe Asp
        35                  40                  45

Pro Gln Glu Pro Thr Cys Leu Gln Thr Arg Leu Glu Leu Tyr Lys Gln
    50                  55                  60

Gly Leu Arg Gly Cys Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125


<210> SEQ ID NO 7
<211> LENGTH: 127
<212> TYPE: PRT
<213> ORGANISM: Artificial Sequence
<220> FEATURE:
<223> OTHER INFORMATION: S29C/S69C/K107I  GM-CSF variant

<400> SEQUENCE: 7

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Cys Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Cys Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Ile Glu Asn Leu Lys Asp
            100                 105                 110

Phe Leu Leu Val Ile Pro Phe Asp Cys Trp Glu Pro Val Gln Glu
        115                 120                 125


<210> SEQ ID NO 8
<211> LENGTH: 127
<212> TYPE: PRT
<213> ORGANISM: Artificial Sequence
<220> FEATURE:
<223> OTHER INFORMATION: S29C/S69C/R23L/L49P/K107I  GM-CSF variant
```

<400> SEQUENCE: 8

Ala Pro Ala Arg Ser Pro Ser Pro Ser Thr Gln Pro Trp Glu His Val
1 5 10 15

Asn Ala Ile Gln Glu Ala Leu Arg Leu Leu Asn Leu Cys Arg Asp Thr
20 25 30

Ala Ala Glu Met Asn Glu Thr Val Glu Val Ile Ser Glu Met Phe Asp
35 40 45

Pro Gln Glu Pro Thr Cys Leu Gln Thr Arg Leu Glu Leu Tyr Lys Gln
50 55 60

Gly Leu Arg Gly Cys Leu Thr Lys Leu Lys Gly Pro Leu Thr Met Met
65 70 75 80

Ala Ser His Tyr Lys Gln His Cys Pro Pro Thr Pro Glu Thr Ser Cys
85 90 95

Ala Thr Gln Ile Ile Thr Phe Glu Ser Phe Ile Glu Asn Leu Lys Asp
100 105 110

Phe Leu Leu Val Ile Pro Phe Asp Cys Trp Glu Pro Val Gln Glu
115 120 125

<210> SEQ ID NO 9
<211> LENGTH: 127
<212> TYPE: PRT
<213> ORGANISM: Artificial Sequence
<220> FEATURE:
<223> OTHER INFORMATION: S29C/S69C/L49P/K107I GM-CSF variant

<400> SEQUENCE: 9

Ala Pro Ala Arg Ser Pro Ser Pro Ser Thr Gln Pro Trp Glu His Val
1 5 10 15

Asn Ala Ile Gln Glu Ala Arg Arg Leu Leu Asn Leu Cys Arg Asp Thr
20 25 30

Ala Ala Glu Met Asn Glu Thr Val Glu Val Ile Ser Glu Met Phe Asp
35 40 45

Pro Gln Glu Pro Thr Cys Leu Gln Thr Arg Leu Glu Leu Tyr Lys Gln
50 55 60

Gly Leu Arg Gly Cys Leu Thr Lys Leu Lys Gly Pro Leu Thr Met Met
65 70 75 80

Ala Ser His Tyr Lys Gln His Cys Pro Pro Thr Pro Glu Thr Ser Cys
85 90 95

Ala Thr Gln Ile Ile Thr Phe Glu Ser Phe Ile Glu Asn Leu Lys Asp
100 105 110

Phe Leu Leu Val Ile Pro Phe Asp Cys Trp Glu Pro Val Gln Glu
115 120 125

<210> SEQ ID NO 10
<211> LENGTH: 387
<212> TYPE: DNA
<213> ORGANISM: Artificial Sequence
<220> FEATURE:
<223> OTHER INFORMATION: S29C/S69C GM-CSF variant DNA

<400> SEQUENCE: 10
gcccccgccc gctcccccte cccatcgacc caaccctggg aacacgtgaa cgccattcag 60
gaggctagga gactgctgaa cctgtgccgg gataccgcag ccgagatgaa cgaaaccgtg 120
gaggtcatct ccgaaatgtt tgacttgcaa gaacctactt gtctgcaaac tcgcctcgag 180
ctgtacaaac agggactccg gggatgtctc actaagctga aggggcctct gaccatgatg 240
gcctcccact acaagcagca ctgcccgccg acgccggaaa ccagctgcgc gacccagatc 300
attaccttcg aatcgttcaa ggaaaacctg aaggacttcc tgcttgtgat cccgttcgac 360
tgctgggagc ctgtgcagga gtgataa 387

<210> SEQ ID NO 11
<211> LENGTH: 387
<212> TYPE: DNA
<213> ORGANISM: Artificial Sequence
<220> FEATURE:
<223> OTHER INFORMATION: L49P GM-CSF variant DNA

<400> SEQUENCE: 11
gcccccgccc gctccccctc cccatcgacc caaccctggg aacacgtgaa cgccattcag 60
gaggctagga gactgctgaa cctgtcccgg gataccgcag ccgagatgaa cgaaaccgtg 120
gaggtcatct ccgaaatgtt tgacccacaa gaacctactt gtctgcaaac tcgcctcgag 180
ctgtacaaac agggactccg ggaagcctc actaagctga aggggcctct gaccatgatg 240
gcctcccact acaagcagca ctgcccgccg acgccggaaa ccagctgcgc gacccagatc 300
attaccttcg aatcgttcaa ggaaaacctg aaggacttcc tgcttgtgat cccgttcgac 360
tgctgggagc ctgtgcagga gtgataa 387

<210> SEQ ID NO 12
<211> LENGTH: 387
<212> TYPE: DNA
<213> ORGANISM: Artificial Sequence
<220> FEATURE:
<223> OTHER INFORMATION: K107I GM-CSF variant DNA

<400> SEQUENCE: 12
gcccccgccc gctccccctc cccatcgacc caaccctggg aacacgtgaa cgccattcag 60
gaggctagga gactgctgaa cctgtcccgg gataccgcag ccgagatgaa cgaaaccgtg 120
gaggtcatct ccgaaatgtt tgacttgcaa gaacctactt gtctgcaaac tcgcctcgag 180
ctgtacaaac agggactccg ggaagcctc actaagctga aggggcctct gaccatgatg 240
gcctcccact acaagcagca ctgcccgccg acgccggaaa ccagctgcgc gacccagatc 300
attaccttcg aatcgttcat cgaaaacctg aaggacttcc tgcttgtgat cccgttcgac 360
tgctgggagc ctgtgcagga gtgataa 387

<210> SEQ ID NO 13
<211> LENGTH: 387
<212> TYPE: DNA
<213> ORGANISM: Artificial Sequence
<220> FEATURE:
<223> OTHER INFORMATION: R23L GM-CSF variant DNA

<400> SEQUENCE: 13
gcccccgccc gctccccctc cccatcgacc caaccctggg aacacgtgaa cgccattcag 60
gaggctctta gactgctgaa cctgtcccgg gataccgcag ccgagatgaa cgaaaccgtg 120
gaggtcatct ccgaaatgtt tgacttgcaa gaacctactt gtctgcaaac tcgcctcgag 180
ctgtacaaac agggactccg ggaagcctc actaagctga aggggcctct gaccatgatg 240
gcctcccact acaagcagca ctgcccgccg acgccggaaa ccagctgcgc gacccagatc 300
attaccttcg aatcgttcaa ggaaaacctg aaggacttcc tgcttgtgat cccgttcgac 360
tgctgggagc ctgtgcagga gtgataa 387

<210> SEQ ID NO 14

<211> LENGTH: 387
<212> TYPE: DNA
<213> ORGANISM: Artificial Sequence
<220> FEATURE:
<223> OTHER INFORMATION: S29C/S69C/L49P GM-CSF variant DNA

<400> SEQUENCE: 14
gcccccgccc gctccccctc cccatcgacc caaccctggg aacacgtgaa cgccattcag 60
gaggctagga gactgctgaa cctgtgccgg gataccgcag ccgagatgaa cgaaaccgtg 120
gaggtcatct ccgaaatgtt tgacccacaa gaacctactt gtctgcaaac tcgcctcgag 180
ctgtacaaac agggactccg gggatgtctc actaagctga aggggcctct gaccatgatg 240
gcctcccact acaagcagca ctgcccgccg acgccggaaa ccagctgcgc gacccagatc 300
attaccttcg aatcgttcaa ggaaaacctg aaggacttcc tgcttgtgat cccgttcgac 360
tgctgggagc ctgtgcagga gtgataa 387

<210> SEQ ID NO 15
<211> LENGTH: 387
<212> TYPE: DNA
<213> ORGANISM: Artificial Sequence
<220> FEATURE:
<223> OTHER INFORMATION: S29C/S69C/K107I GM-CSF variant DNA

<400> SEQUENCE: 15
gcccccgccc gctccccctc cccatcgacc caaccctggg aacacgtgaa cgccattcag 60
gaggctagga gactgctgaa cctgtgccgg gataccgcag ccgagatgaa cgaaaccgtg 120
gaggtcatct ccgaaatgtt tgacttgcaa gaacctactt gtctgcaaac tcgcctcgag 180
ctgtacaaac agggactccg gggatgtctc actaagctga aggggcctct gaccatgatg 240
gcctcccact acaagcagca ctgcccgccg acgccggaaa ccagctgcgc gacccagatc 300
attaccttcg aatcgttcat cgaaaacctg aaggacttcc tgcttgtgat cccgttcgac 360
tgctgggagc ctgtgcagga gtgataa 387

<210> SEQ ID NO 16
<211> LENGTH: 387
<212> TYPE: DNA
<213> ORGANISM: Artificial Sequence
<220> FEATURE:
<223> OTHER INFORMATION: S29C/S69C/R23L/L49P/K107I GM-CSF variant DNA

<400> SEQUENCE: 16
gcccccgccc gctccccctc cccatcgacc caaccctggg aacacgtgaa cgccattcag 60
gaggctttga gactgctgaa cctgtgccgg gataccgcag ccgagatgaa cgaaaccgtg 120
gaggtcatct ccgaaatgtt tgacccacaa gaacctactt gtctgcaaac tcgcctcgag 180
ctgtacaaac agggactccg gggatgcctc actaagctga aggggcctct gaccatgatg 240
gcctcccact acaagcagca ctgcccgccg acgccggaaa ccagctgcgc gacccagatc 300
attaccttcg aatcgttcat cgaaaacctg aaggacttcc tgcttgtgat cccgttcgac 360
tgctgggagc ctgtgcagga gtgataa 387

<210> SEQ ID NO 17
<211> LENGTH: 387
<212> TYPE: DNA
<213> ORGANISM: Artificial Sequence
<220> FEATURE:
<223> OTHER INFORMATION: S29C/S69C/L49P/K107I GM-CSF variant DNA

<400> SEQUENCE: 17
gcccccgccc gctccccctc cccatcgacc caaccctggg aacacgtgaa cgccattcag 60
gaggctagga gactgctgaa cctgtgccgg gataccgcag ccgagatgaa cgaaaccgtg 120
gaggtcatct ccgaaatgtt tgacccacaa gaacctactt gtctgcaaac tcgcctcgag 180
ctgtacaaac agggactccg gggatgtctc actaagctga aggggcctct gaccatgatg 240
gcctcccact acaagcagca ctgcccgccg acgccggaaa ccagctgcgc gacccagatc 300
attaccttcg aatcgttcat cgaaaacctg aaggacttcc tgcttgtgat cccgttcgac 360
tgctgggagc ctgtgcagga gtgataa 387

<210> SEQ ID NO 18
<211> LENGTH: 384
<212> TYPE: DNA
<213> ORGANISM: Homo sapiens

<400> SEQUENCE: 18
gcccccgccc gctccccctc cccatcgacc caaccctggg aacacgtgaa cgccattcag 60
gaggctagga gactgctgaa cctgtcccgg gataccgcag ccgagatgaa cgaaaccgtg 120
gaggtcatct ccgaaatgtt tgacttgcaa gaacctactt gtctgcaaac tcgcctcgag 180
ctgtacaaac agggactccg gggaagcctc actaagctga aggggcctct gaccatgatg 240
gcctcccact acaagcagca ctgcccgccg acgccggaaa ccagctgcgc gacccagatc 300
attaccttcg aatcgttcaa ggaaaacctg aaggacttcc tgcttgtgat cccgttcgac 360
tgctgggagc ctgtgcagga gtaa 384

<210> SEQ ID NO 19
<211> LENGTH: 19
<212> TYPE: PRT
<213> ORGANISM: Artificial Sequence
<220> FEATURE:
<223> OTHER INFORMATION: Signal sequence

<400> SEQUENCE: 19

Met Ala Trp Val Trp Thr Leu Leu Phe Leu Met Ala Ala Ala Gln Ser
1               5                   10                  15

Ile Gln Ala

<210> SEQ ID NO 20
<211> LENGTH: 38
<212> TYPE: PRT
<213> ORGANISM: Artificial Sequence
<220> FEATURE:
<223> OTHER INFORMATION: 1FU1 linker

<400> SEQUENCE: 20

Ala Ser Leu Asp Thr Thr Ala Glu Asn Gln Ala Lys Asn Glu His Leu
1               5                   10                  15

Gln Lys Glu Asn Glu Arg Leu Leu Arg Asp Trp Asn Asp Val Gln Gly
            20                  25                  30

Arg Phe Glu Lys Gly Ser
        35

<210> SEQ ID NO 21
<211> LENGTH: 30
<212> TYPE: PRT
<213> ORGANISM: Artificial Sequence
<220> FEATURE:
<223> OTHER INFORMATION: 1DC1(13AA)2 linker

<400> SEQUENCE: 21

Ala Ser Glu Lys Asn Lys Arg Ser Thr Pro Tyr Ile Glu Arg Ala Glu
1 5 10 15

Lys Asn Lys Arg Ser Thr Pro Tyr Ile Glu Arg Ala Gly Ser
20 25 30

<210> SEQ ID NO 22
<211> LENGTH: 43
<212> TYPE: PRT
<213> ORGANISM: Artificial Sequence
<220> FEATURE:
<223> OTHER INFORMATION: 1DC1(13AA)3 linker

<400> SEQUENCE: 22

Ala Ser Glu Lys Asn Lys Arg Ser Thr Pro Tyr Ile Glu Arg Ala Glu
1 5 10 15

Lys Asn Lys Arg Ser Thr Pro Tyr Ile Glu Arg Ala Glu Lys Asn Lys
20 25 30

Arg Ser Thr Pro Tyr Ile Glu Arg Ala Gly Ser
35 40

<210> SEQ ID NO 23
<211> LENGTH: 24
<212> TYPE: PRT
<213> ORGANISM: Artificial Sequence
<220> FEATURE:
<223> OTHER INFORMATION: AS(AP)10GS linker

<400> SEQUENCE: 23

Ala Ser Ala Pro Ala Pro Ala Pro Ala Pro Ala Pro Ala Pro Ala Pro
1 5 10 15

Ala Pro Ala Pro Ala Pro Gly Ser
20

<210> SEQ ID NO 24
<211> LENGTH: 44
<212> TYPE: PRT
<213> ORGANISM: Artificial Sequence
<220> FEATURE:
<223> OTHER INFORMATION: AS(AP)20GS linker

<400> SEQUENCE: 24

Ala Ser Ala Pro Ala Pro Ala Pro Ala Pro Ala Pro Ala Pro Ala Pro
1 5 10 15

Ala Pro Ala Pro Ala Pro Ala Pro Ala Pro Ala Pro Ala Pro Ala Pro
20 25 30

Ala Pro Ala Pro Ala Pro Ala Pro Ala Pro Gly Ser
35 40

<210> SEQ ID NO 25
<211> LENGTH: 26
<212> TYPE: PRT
<213> ORGANISM: Artificial Sequence
<220> FEATURE:
<223> OTHER INFORMATION: (EAAAK)4 linker

<400> SEQUENCE: 25

Ala Ser Ala Glu Ala Ala Ala Lys Glu Ala Ala Ala Lys Glu Ala Ala
1 5 10 15

Ala Lys Glu Ala Ala Ala Lys Ala Gly Ser
20 25

<210> SEQ ID NO 26
<211> LENGTH: 46
<212> TYPE: PRT
<213> ORGANISM: Artificial Sequence
<220> FEATURE:
<223> OTHER INFORMATION: (EAAAK)8 linker

<400> SEQUENCE: 26

```
Ala Ser Ala Glu Ala Ala Ala Lys Glu Ala Ala Ala Lys Glu Ala Ala
1               5                   10                  15

Ala Lys Glu Ala Ala Ala Lys Glu Ala Ala Ala Lys Glu Ala Ala Ala
            20                  25                  30

Lys Glu Ala Ala Ala Lys Glu Ala Ala Ala Lys Ala Gly Ser
        35                  40                  45
```

<210> SEQ ID NO 27
<211> LENGTH: 22
<212> TYPE: PRT
<213> ORGANISM: Artificial Sequence
<220> FEATURE:
<223> OTHER INFORMATION: GS(G4S)4 linker

<400> SEQUENCE: 27

```
Gly Ser Gly Gly Gly Gly Ser Gly Gly Gly Gly Ser Gly Gly Gly Gly
1               5                   10                  15

Ser Gly Gly Gly Gly Ser
            20
```

<210> SEQ ID NO 28
<211> LENGTH: 42
<212> TYPE: PRT
<213> ORGANISM: Artificial Sequence
<220> FEATURE:
<223> OTHER INFORMATION: GS(G4S)8 linker

<400> SEQUENCE: 28

```
Gly Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser
        35                  40
```

<210> SEQ ID NO 29
<211> LENGTH: 62
<212> TYPE: PRT
<213> ORGANISM: Artificial Sequence
<220> FEATURE:
<223> OTHER INFORMATION: GS12X(G4S) linker

<400> SEQUENCE: 29

```
Gly Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser Gly Gly Gly Gly Ser Gly
        35                  40                  45

Gly Gly Gly Ser Gly Gly Gly Gly Ser Gly Gly Gly Gly Ser
    50                  55                  60
```

<210> SEQ ID NO 30
<211> LENGTH: 82
<212> TYPE: PRT

<213> ORGANISM: Artificial Sequence
<220> FEATURE:
<223> OTHER INFORMATION: GS16X(G4S) linker

<400> SEQUENCE: 30

```
Gly Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser Gly Gly Gly Gly Ser Gly
        35                  40                  45

Gly Gly Gly Ser Gly Gly Gly Gly Ser Gly Gly Gly Gly Ser Gly Gly
    50                  55                  60

Gly Gly Ser Gly Gly Gly Gly Ser Gly Gly Gly Gly Ser Gly Gly Gly
65                  70                  75                  80

Gly Ser
```

<210> SEQ ID NO 31
<211> LENGTH: 19
<212> TYPE: PRT
<213> ORGANISM: Homo sapiens

<400> SEQUENCE: 31

```
Met Ala Trp Val Trp Thr Leu Leu Phe Leu Met Ala Ala Ala Gln Ser
1               5                   10                  15

Ile Gln Ala
```

<210> SEQ ID NO 32
<211> LENGTH: 57
<212> TYPE: DNA
<213> ORGANISM: Homo sapiens

<400> SEQUENCE: 32

```
atggcctggg tgtggaccct gctgttcctg atggccgccg cccagagcat ccaggcc        57
```

<210> SEQ ID NO 33
<211> LENGTH: 127
<212> TYPE: PRT
<213> ORGANISM: Artificial Sequence
<220> FEATURE:
<223> OTHER INFORMATION: Genus sequence
<220> FEATURE:
<221> NAME/KEY: MISC_FEATURE
<222> LOCATION: (23)..(23)
<223> OTHER INFORMATION: Xaa may be R or L
<220> FEATURE:
<221> NAME/KEY: MISC_FEATURE
<222> LOCATION: (49)..(49)
<223> OTHER INFORMATION: Xaa may be L or P
<220> FEATURE:
<221> NAME/KEY: MISC_FEATURE
<222> LOCATION: (107)..(107)
<223> OTHER INFORMATION: Xaa may be K or I

<400> SEQUENCE: 33

```
Ala Pro Ala Arg Ser Pro Ser Pro Ser Thr Gln Pro Trp Glu His Val
1               5                   10                  15

Asn Ala Ile Gln Glu Ala Xaa Arg Leu Leu Asn Leu Cys Arg Asp Thr
            20                  25                  30

Ala Ala Glu Met Asn Glu Thr Val Glu Val Ile Ser Glu Met Phe Asp
        35                  40                  45

Xaa Gln Glu Pro Thr Cys Leu Gln Thr Arg Leu Glu Leu Tyr Lys Gln
    50                  55                  60
```

-continued

```
Gly Leu Arg Gly Cys Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Xaa Glu Asn Leu Lys Asp
            100                 105                 110

Phe Leu Leu Val Ile Pro Phe Asp Cys Trp Glu Pro Val Gln Glu
        115                 120                 125
```